(12) United States Patent
Guth et al.

(10) Patent No.: US 6,306,378 B1
(45) Date of Patent: Oct. 23, 2001

(54) CATALYZED WATER-SOLUBLE/ DISPERSIBLE REACTIVE DERIVATIVES OF POLYIMIDO COMPOUNDS FOR MODIFYING PROTEINACEOUS SUBSTRATES

(75) Inventors: Jacob J. Guth, Upper Black Eddy, PA (US); Samuel A. Vona, Jr., Bound Brook; John S. Thomaides, Berkeley Heights, both of NJ (US); Ann C. Savoca, Nazareth, PA (US)

(73) Assignee: National Starch & Chemical Investment Holding Corp., Wilmington, DE (US)

( * ) Notice: Subject to any disclaimer, the term of this patent is extended or adjusted under 35 U.S.C. 154(b) by 0 days.

(21) Appl. No.: 09/287,900

(22) Filed: Apr. 7, 1999

Related U.S. Application Data

(63) Continuation-in-part of application No. 09/218,846, filed on Dec. 22, 1998.

(51) Int. Cl.[7] .............. A61K 7/11; A61K 31/74; C07D 207/40
(52) U.S. Cl. ............ 424/70.1; 424/70.2; 424/70.4; 424/70.6; 424/70.9; 424/70.11; 424/70.122; 424/70.13; 424/70.17; 424/78.03; 424/400; 424/401; 548/485; 548/486; 548/546; 548/547; 564/153
(58) Field of Search .................... 424/70.1, 70.2, 424/70.4, 70.6, 70.9, 70.11, 70.122, 70.13, 70.17, 78.03, 400, 401; 548/485–6, 546–7; 564/153

(56) References Cited

U.S. PATENT DOCUMENTS

| | | |
|---|---|---|
| 4,279,996 | 7/1981 | Yoshioka et al. .......... 435/69 |
| 4,314,808 | 2/1982 | Jacquet et al. ............ 8/405 |
| 4,363,797 | 12/1982 | Jacquet et al. ............ 424/70 |
| 4,735,797 | 4/1988 | Grollier et al. ............ 424/47 |
| 5,175,285 | * 12/1992 | Lehmann et al. .......... 544/141 |
| 5,686,066 | * 11/1997 | Harada et al. ............ 424/70.14 |

FOREIGN PATENT DOCUMENTS

| | | |
|---|---|---|
| 78-12516 | 4/1978 | (FR) . |
| 8-258688 | 9/1996 | (JP) . |

OTHER PUBLICATIONS

Chemical Abstracts 127:39464v (Matsuzawa et al., 1997).

* cited by examiner

*Primary Examiner*—Jose' G. Dees
*Assistant Examiner*—Kathryne E. Shelborne
(74) *Attorney, Agent, or Firm*—Richard R. Muccino

(57) ABSTRACT

This invention relates to a two-part system useful for treating proteinaceous substrates. The two-part system has a first part comprising a water-soluble/dispersible reactive polyimido compound and a second part comprising a nucleophilic catalytic agent. The polyimido compounds may be selected from the group consisting of polysuccinimide compounds, polyglutimide compounds, and copolymers of thereof. The polyimido compound may also comprise a functionalizing moiety that provides functionality to the polyimido compound and is preferably derived from a nucleophilic moiety selected from the group consisting of amines, alcohols, phenols, thiols, and carboxylates; and a water-solubilizing/dispersing moiety that provides water-solubility and/or water-dispersibility to the polyimido compound and is preferably derived from a nucleophilic moiety selected from the group consisting of amines, alcohols, phenols, thiols, and carboxylates. The nucleophilic catalytic agent serves to catalyze nuclephilic substitution of the polyimido compound by the proteinaceous substrate. The invention also pertains to a method for treating a proteinaceous substrate with the two-part system and to a composition comprising a mixture of the polyimido compound and the nucleophilic catalytic agent.

41 Claims, No Drawings

CATALYZED WATER-SOLUBLE/DISPERSIBLE REACTIVE DERIVATIVES OF POLYIMIDO COMPOUNDS FOR MODIFYING PROTEINACEOUS SUBSTRATES

This invention is a continuation-in-part application of application Ser. No. 09/218,846, filed Dec. 22, 1998.

BACKGROUND OF THE INVENTION

1. Field of the Invention

This invention relates to a two-part system useful for treating proteinaceous substrates. The two-part system has a first part comprising a water-soluble/dispersible reactive polyimido compound and a second part comprising a nucleophilic catalytic agent. The polyimido compounds may be selected from the group consisting of polysuccinimide compounds, polyglutimide compounds, and copolymers of thereof. The polyimido compound may also comprise a functionalizing moiety that provides functionality to the polyimido compound and is preferably derived from a nucleophilic moiety selected from the group consisting of amines, alcohols, phenols, thiols, and carboxylates; and a water-solubilizing/dispersing moiety that provides water-solubility and/or water-dispersibility to the polyimido compound and is preferably derived from a nucleophilic moiety selected from the group consisting of amines, alcohols, phenols, thiols, and carboxylates. The nucleophilic catalytic agent is believed to catalyze nuclephilic substitution of the polyimido compound by the proteinaceous substrate. The invention also pertains to a method for treating a proteinaceous substrate with the two-part system and to a composition comprising a mixture of the polyimido compound and the nucleophilic catalytic agent.

2. Description of the Background

Hair is a proteinaceous substrate containing protein chains connected by sulfur-sulfur cross-linkages from cystine. When hair is bleached or permed, the cystine disulfide bonds are cleaved, typically with sodium thioglycolate, sodium sulfite, or some other disulfide bond-cleaving agent. The hair is then put into a curled or straightened state, whichever is desired, and the disulfide bonds are then allowed to reform. New sulfur-sulfur cross-linkages between the protein chains are formed thus locking the hair into the new array. In practice, not all of the disulfide bonds reform by oxidation. This cleavage of the sulfur-sulfur cross-linkages results in a weakening of the hair making it more susceptible to breakage during combing and brushing. In addition, because perming formulations are generally very alkaline, some amide linkages in the protein chains are also cleaved resulting in a further weakening of the hair. Currently, there is no cosmetically acceptable method of improving strength by imparting additional cross-linkages to hair. Moreover, both the strength of the hair and the combing properties of the hair are adversely affected by the perming/bleaching process. Conventional treatments to improve the combing properties include various conditioning agents. However, because these conditioning agents do not covalently bond to hair, their conditioning effects are removed by washing and must be repeatedly applied. Improved shine and gloss, UV protection, anti-stat properties, anti-microbial protection, color, as well as many other improvements, which are desirable to intact and/or damaged hair, all suffer from a lack of permanence on hair and must be continually replenished.

While there are many disclosures that describe compositions useful for modifying proteinaceous substrates, including one-step oxidation dye compositions (The Science of Hair Care, Charles Zviak, Ed., Marcel Dekker, 1986; pp. 133 et seq.; Chemical And Physical Behavior of Hair, Clarence R. Robbins, Van Nostrand Reinhold Company, 1979, pp. 276–279), none of the disclosures describe compositions that are entirely satisfactory. None of the disclosures describe the preparation of catalyzed water-soluble or water-dispersible reactive polyimido compounds that can be covalently and permanently bonded to a proteinaceous substrate. The present invention provides such improved catalyzed water-soluble or water-dispersible polyimido compounds, many of which, upon reaction, revert to biodegradable and environmentally friendly compounds.

SUMMARY OF THE INVENTION

This invention relates to a two-part system useful for treating a proteinaceous substrate which comprises a first part comprising a polyimido compound and a second part comprising an aqueous solution of a nucleophilic catalytic agent, wherein the pH value of the aqueous solution of nucleophilic catalytic agent is such that when the aqueous nucleophilic catalytic agent is mixed with the polyimido compound, the resulting mixture will have a pH in a range sufficient to enable the nucleophilic catalytic agent to react with the polyimido compound;

wherein the polyimido compound is selected from the group consisting of polysuccinimide compounds represented by Formula (1):

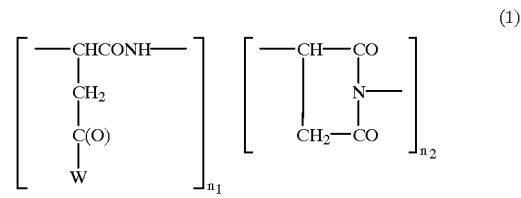

(1)

polyglutimide compounds represented by Formula (2);

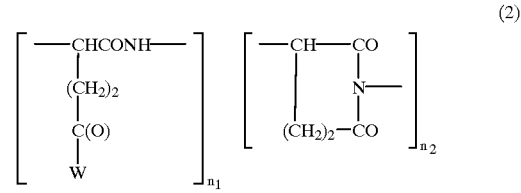

(2)

polysuccinimide compounds represented by Formula (3):

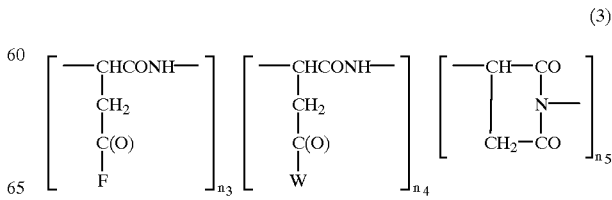

(3)

polyglutimide compounds represented by Formula (4);

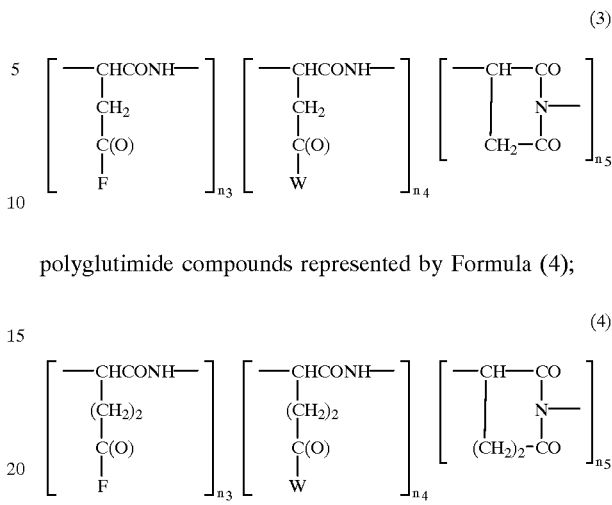

copolymers of the polysuccinimide compounds represented by Formula (1) with the polyglutimide compounds represented by Formula (2); and copolymers of the polysuccinimide compounds represented by Formula (3) with the polyglutimide compounds represented by Formula (4);

wherein W is a water-solubilizing/dispersing moiety that provides water-solubility and/or water-dispersibility to the polyimido compound; F is a functionalizing moiety that provides functionality to the polyimido compound; the ratio of $n_1$ to $n_2$ is from about 1:99 to about 99:1; the ratio of $n_3:n_4:n_5$ is from about 1:1:98 to about 45:45:10; and the molecular weight of the polyimido compound is from about 300 to about 1,000,000.

This invention also pertains to a method for treating a proteinaceous substrate which comprises the steps of:

(a) contacting a polyimido compound with an aqueous solution of an nucleophilic catalytic agent to form a mixture, wherein the pH value of the aqueous solution of nucleophilic catalytic agent is such that when the aqueous nucleophilic catalytic agent is mixed with the polyimido compound, the resulting mixture will have a pH in a range sufficient to enable the nucleophilic catalytic agent to react with the polyimido compound; and (b) contacting the mixture from step (a) with a proteinaceous substrate for a time sufficient to allow the mixture to react with the proteinaceous substrate;

wherein the polyimido compound is selected from the group consisting of polysuccinimide compounds represented by Formula (1):

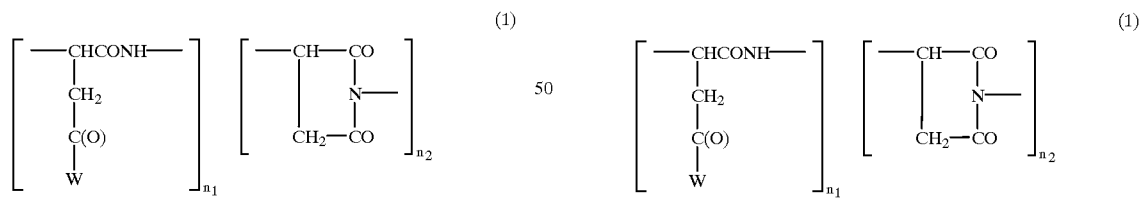

polyglutimide compounds represented by Formula (2);

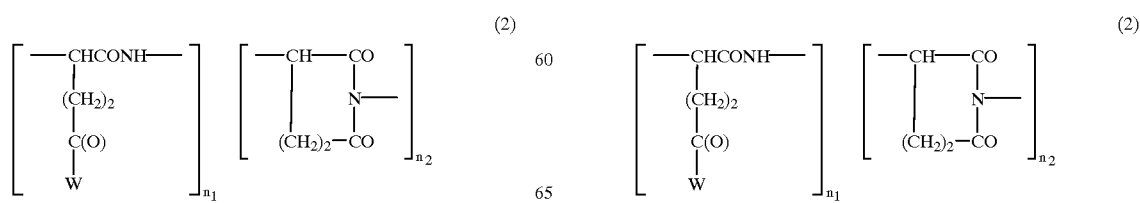

polysuccinimide compounds represented by Formula (3):

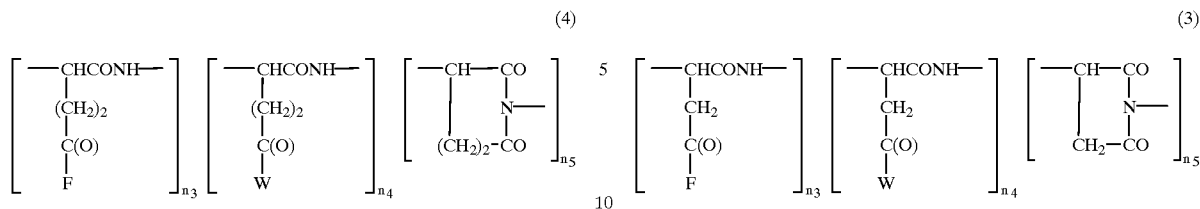

polyglutimide compounds represented by Formula (4);

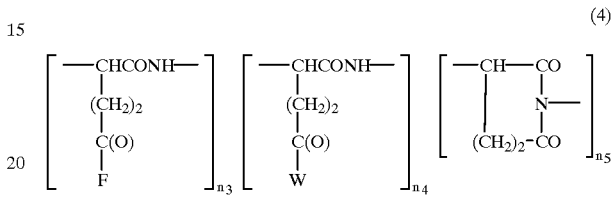

copolymers of the polysuccinimide compounds represented by Formula (1) with the polyglutimide compounds represented by Formula (2); and copolymers of the polysuccinimide compounds represented by Formula (3) with the polyglutimide compounds represented by Formula (4);

wherein W is a water-solubilizing/dispersing moiety that provides water-solubility and/or water-dispersibility to the polyimido compound; F is a functionalizing moiety that provides functionality to the polyimido compound; the ratio of $n_1$ to $n_2$ is from about 1:99 to about 99:1; the ratio of $n_3:n_4:n_5$ is from about 1:1:98 to about 45:45:10; and the molecular weight of the polyimido compound is from about 300 to about 1,000,000.

This invention also pertains to a composition useful for treating a proteinaceous substrate which comprises an aqueous mixture of a polyimido compound and a nucleophilic catalytic agent having a pH value in a range sufficient to enable the nucleophilic catalytic agent to react with the polyimido compound;

wherein the polyimido compound is selected from the group consisting of polysuccinimide compounds represented by Formula (1):

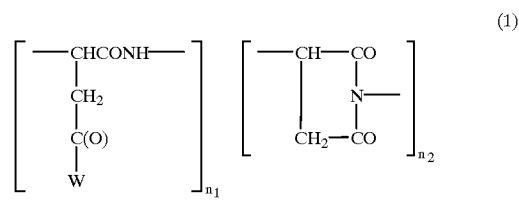

polyglutimide compounds represented by Formula (2);

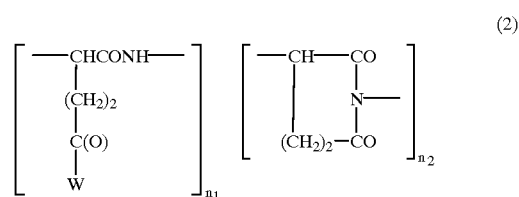

polysuccinimide compounds represented by Formula (3):

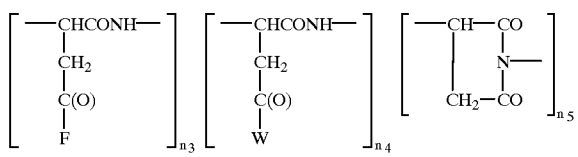

polyglutimide compounds represented by Formula (4);

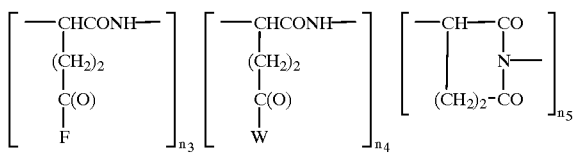

copolymers of the polysuccinimide compounds represented by Formula (1) with the polyglutimide compounds represented by Formula (2); and copolymers of the polysuccinimide compounds represented by Formula (3) with the polyglutimide compounds represented by Formula (4);
wherein W is a water-solubilizing/dispersing moiety that provides water-solubility and/or water-dispersibility to the polyimido compound; F is a functionalizing moiety that provides functionality to the polyimido compound; the ratio of $n_1$ to $n_2$ is from about 1:99 to about 99:1; the ratio of $n_3:n_4:n_5$ is from about 1:1:98 to about 45:45:10; and the molecular weight of the polyimido compound is from about 300 to about 1,000,000.

This invention also pertains to a method for treating a proteinaceous substrate which comprises the steps of:

(a) contacting an imido or polyimido compound with an aqueous solution of an nucleophilic catalytic agent to form a mixture, wherein the pH value of the aqueous solution of nucleophilic catalytic agent is such that when the aqueous nucleophilic catalytic agent is mixed with the imido or polyimido compound, the resulting mixture will have a pH in a range sufficient to enable the nucleophilic catalytic agent to react with the imido or polyimido compound; wherein the imido or polyimido compound has attached thereto a functionalizing moiety F that provides functionality to the imido or polyimido compound; and (b) contacting the mixture from step (a) with a proteinaceous substrate for a time sufficient to allow the mixture to react with the proteinaceous substrate.

DETAILED DESCRIPTION OF THE INVENTION

The present invention is directed to catalyzed water-soluble/dispersible reactive derivatives of polyimido compounds useful for modifying proteinaceous substrates such as hair, wool, skin, leather, silk, fur, felt, and nails. Applicants have found that reaction of a portion of the imide groups in the water-insoluble polysuccinimide (or polyglutimide) with a water-solubilizing/dispersing nucleophilic agent yields a water-soluble/dispersible polymer containing reactive sites at the remaining imide moieties. This water-soluble/dispersible polyimide, containing reactive imide moieties, is a water-soluble/dispersible acylating agent which can now be covalently and permanently reacted with various nucleophilic groups present on the proteinaceous substrate to impart permanent changes to these substrates. Alternatively, a portion of the imide groups in the water-insoluble polysuccinimide (or polyglutimide) can be reacted with a functionalizing group followed by reaction of another portion of the imide groups with a water-solubilizing nucleophilic agent to yield a water-soluble/dispersible functionalized polymer containing reactive sites at the remaining imide moieties. Examples of suitable functionalizing groups include antimicrobials, ultraviolet chromophores, dyes, anti-oxidants, fluorescing agents, brightening agents, shine and gloss enhancers, softening agents, conditioning agents, and water-repellants. Because of the unique and unexpected properties of the polyimido acylating agents of the present invention, the polyimido compounds, with or without a functionalizing group, can be used in applications to provide permanent modification of proteinaceous substrates such as hair and skin under aqueous conditions. In another embodiment, the polyimido acylating agents can be further reacted with a multifunctional nucleophilic agent to promote the development of cross-linked polymers to further modify the proteinaceous substrate. In yet another embodiment, the proteinaceous substrate may be bonded to a polyimido acylating agent having a water-solubilizing/dispersing moiety bearing a strong ionic charge which can electrostatically bind to moieties bearing the opposite charge. By priming the proteinaceous substrate with a highly charged polymer, one can modify the surface of the proteinaceous substrate to make it attract chemical moieties of the opposite charge and thereby impart a wide variety of beneficial properties to the proteinaceous substrate. Moreover, many of the polyimido compounds, upon hydrolysis, revert to biodegradable and environmentally friendly compounds.

In a specific embodiment, the present invention is directed to a two-part system having a first part comprising a water-soluble/dispersible reactive derivative of a polyimido compound and a second part comprising an aqueous solution of a nucleophilic catalytic agent. The pH value of the aqueous solution of nucleophilic catalytic agent is such that when the aqueous nucleophilic catalytic agent is mixed with the polyimido compound, the resulting mixture will have a pH in a range sufficient to enable the nucleophilic catalytic agent to react with the polyimido compound. Applicants have found that when the polyimido compound is mixed with the nucleophilic catalytic agent, just prior to use, the resulting catalyzed polyimido compound reacts more efficiently with nucleophilic groups present on a proteinaceous substrate than a polyimido compound not mixed with a nucleophilic catalytic agent. Applicants believe that the nucleophilic catalytic agents may function by a two-step mechanism, wherein a nucleophilic catalytic agent first reacts with a carbonyl group present in the polyimido compound to form a reactive intermediate, followed by displacement of the nucleophilic catalytic agent from the carbonyl group in the polyimido compound by a nucleophilic group present in the proteinaceous substrate.

Moreover, mixture of applicants' two-part system provides a one-step method useful for treating proteinaceous substrates which is consumer friendly and more likely to result in consumer acceptance. Specifically, the inventive method comprises contacting a polyimido compound with a nucleophilic catalytic agent, having a pH value in a range sufficient to enable the nucleophilic catalytic agent to react with the polyimido compound, to form a mixture, followed by contacting the resulting mixture with a proteinaceous substrate for a time sufficient to allow the mixture to react with the proteinaceous substrate.

Condensation of aspartic acid in the presence of an acid catalyst such as $H_3PO_4$ yields the water-insoluble polysuccinimide.

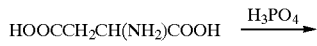

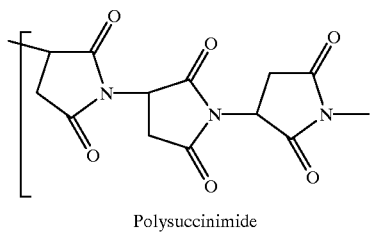

Polysuccinimide

Partial reaction of the succinimide groups in polysuccinimide with a water-solubilizing/dispersing nucleophilic agent (W), usually carried out in an aprotic solvent such as dimethylsulfoxide, sulfolane, or dimethylformamide, results in the formation of a water-soluble/dispersible polymer containing reactive sites at the remaining succinimide moieties.

(1)

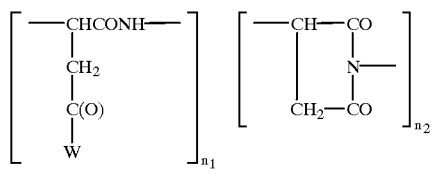

Alternatively, partial reaction of the succinimide groups in polysuccinimide with a nucleophilic functionalizing agent (F) in an aprotic solvent results in the formation of a functionalized polymer containing reactive sites at the remaining succinimide moieties.

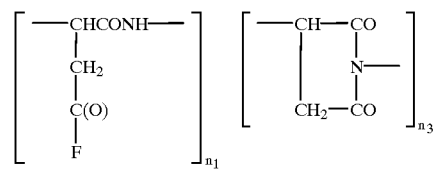

Further partial reaction of the succinimide groups in the functionalized polysuccinimide with a nucleophilic water-solubilizing agent (W) in an aprotic solvent results in the formation of a water-soluble/dispersible functionalized polymer still containing reactive sites at the remaining succinimide moieties.

(3)

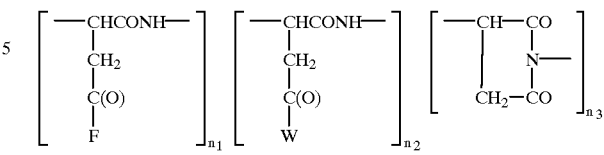

In accord with the present invention, a polyimido compound is provided which is selected from the group consisting of polysuccinimide compounds represented by Formula (1):

(1)

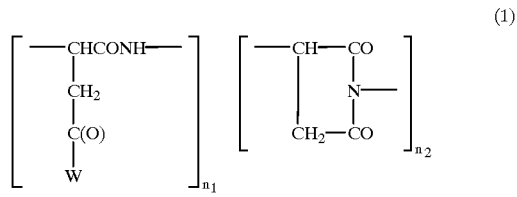

polyglutimide compounds represented by Formula (2);

(2)

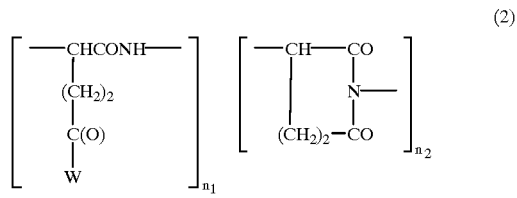

polysuccinimide compounds represented by Formula (3):

(3)

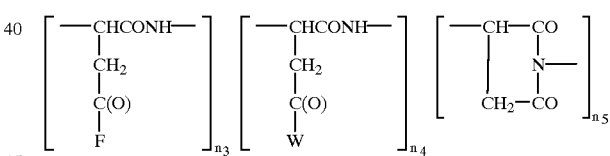

polyglutimide compounds represented by Formula (4);

(4)

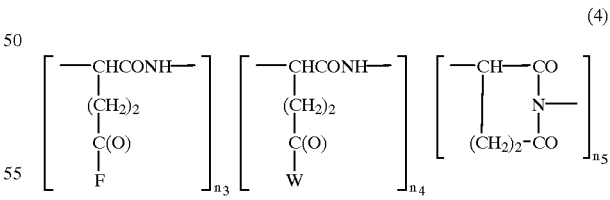

copolymers of the polysuccinimide compounds represented by Formula (1) with the polyglutimide compounds represented by Formula (2); and copolymers of the polysuccinimide compounds represented by Formula (3) with the polyglutimide compounds represented by Formula (4).

In Formulae (1) to (4), W is a water-solubilizing/dispersing moiety that provides water-solubility and/or water-dispersibility to the polyimido compound. The water-solubilizing/dispersing moieties which may be employed in the present invention include all moieties which can covalently react with the polyimido compound and provide water-solubility and/or water-dispersibility to the polyimido compound. In a preferred embodiment, the nucleophilic water-solubilizing/dispersing moieties may be derived from a nucleophilic moiety selected from the group consisting of amines, alcohols, phenols, thiols, and carboxylates. Preferably, W is the result of reacting a polyimido compound with an amine.

Preferred water-solubilizing/dispersing moieties may be selected from the group of nucleophiles consisting of:

(1) aminopolysaccharides preferably represented by the formula, $-N(R_1)$-polysaccharide, wherein $R_1$ is hydrogen or lower alkyl ($C_1$ to $C_5$) and the number of units in the polysaccharide ranges from 1 to about 51. Substitution of from about 0.10 to about 0.80 equivalents of the polysaccharide, based on the available imide moieties, is generally required for solubilization. An example of a polyimido compound containing a maltodextrin aminopolysaccharide water-solubilizing/dispersing moiety is set out below.

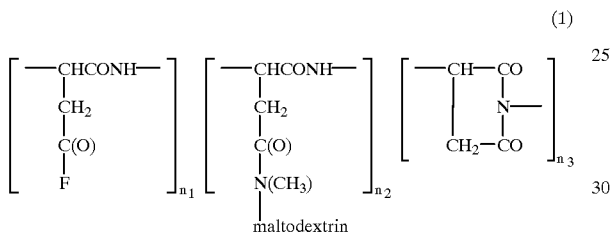

(1)

maltodextrin (2) amines containing quaternary ammonium salts preferably represented by the formula, $[-N(R_1)(CH_2)_{n_3}N^{30}(CH_3)_3][A^-]$, wherein $R_1$ is hydrogen or lower alkyl ($C_1$ to $C_5$), $n_3$ is an integer from 1 to about 10, preferably from 1 to about 7, and A is a monovalent anion. Substitution of from about 0.10 to about 0.80 equivalents of the amino containing quaternary ammonium salt, based on the available imide moieties, is generally required for solubilization. An example of a polyimido compound containing an amino containing quaternary ammonium salt water-solubilizing/dispersing moiety is set out below.

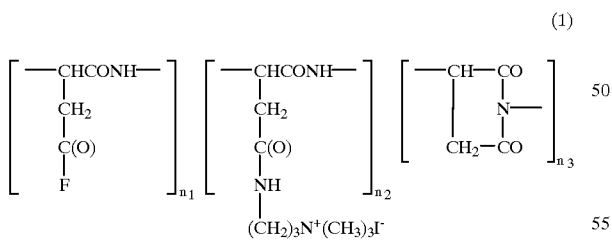

(1)

(3) amines containing alcohols preferably represented by the formula, $-N(R_1)(CH_2)_{n_4}OH$, wherein $R_1$ is hydrogen or lower alkyl ($C_1$ to $C_5$) and $n_4$ is an integer from 2 to about 10, preferably from 2 to about 7. Substitution of from about 0.10 to about 0.80 equivalents of the amino containing alcohol, based on available imide moieties, is generally required for solubilization. An example of a polyimido compound containing an amino containing alcohol water-solubilizing/dispersing moiety is set out below.

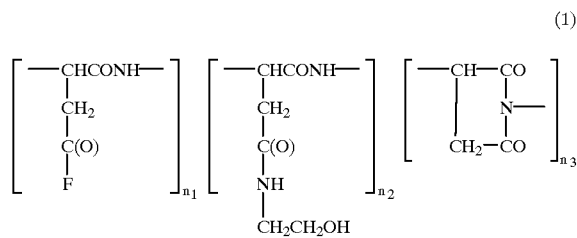

(1)

(4) amines containing polyalkoxylated alcohols preferably represented by the formula, $-N(R_1)CH(CH_3)$ $CH_2-(OCHR_2CH_2)_{n_5}-OCH_3$, wherein $R_1$ is hydrogen or lower alkyl ($C_1$ to $C_5$), $R_2$ may be hydrogen or methyl, and $n_5$ is an integer from 0 to about 50, preferably from 0 to about 35. Substitution of from about 0.10 to about 0.80 equivalents of the amino containing polyalkoxylated alcohol, based on available imide moieties, is generally required for solubilization.

(5) thiols containing alcohols preferably represented by the formula, $-S(CH_2)_{n_6}OH$, wherein $n_6$ is an integer ranging from 2 to about 10 preferably from 3 to about 7. Substitution of from about 0.10 to about 0.80 equivalents of the thiol terminated compound, based on available imide moieties, is generally required for solubilization.

(6) alcohols containing ethers preferably represented by the formula, $-O(CH_2CH_2O)_{n_7}OM$, wherein $n_7$ is an integer ranging from 0 to about 50, preferably from 0 to about 35, and M is an alkyl group containing from 1 to about 30 carbons, preferably from 1 to about 20,. Substitution of from about 0.10 to about 0.80 equivalents of the hydroxyl terminated compound, based on available imide moieties, is generally required for solubilization.

(7) $-O^-X^+$, where X is selected from the group consisting of $H^+$, $Na^+$, $Li^+$, $NH_4^+$, $NH(CH_3)_3^+$; $NH_3$ $(CH_2CH_2OH)^+$, $NH_2(CH_2CH_2OH)_2^+$, and $NH(CH_2CH_2OH)_3^+$; such as when the water-solubilizing/dispersing moiety is the result of ring opening of some of the imide groups with aqueous bases such as NaOH or $NH_4OH$. An example of a polyimido compound containing this type of water-solubilizing/dispersing moiety is set out below.

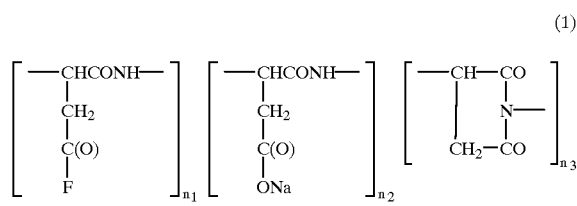

(1)

(8) $[-NH(CH_2)_3N^+(CH_3)_2CH_2COONa][A^-]$, $[-NH(CH_2)_3N^+(CH_3)_2CH_2COO2-]$, $-N(CH_3)(CH_2)_2SO_3Na$ (N-methyltaurine), and $-NH(CH_2)_2SO_3Na$ (taurine), wherein A is a monovalent anion, including other anionic, amphoteric, or zwitterionic water-solubilizing groups.

In Formulae (3) and (4), F is a functionalizing moiety that provides functionality to the polyimido compound. The functionalizing moieties which may be employed in the present invention include all moieties which can covalently react with the polyimido compound and provide functionality to the polyimido compound and allow modification of a proteinaceous substrate. In a preferred embodiment, the functionalizing moieties may be derived from a nucleophilic moiety selected from the group consisting of amines, alcohols, phenols, thiols, and carboxylates. Preferably, F is the result of reacting a polyimide compound with an amine. Preferred functionalizing moieties may be selected from the group of nucleophiles consisting of antimicrobials, ultraviolet chromophores, dyes, anti-oxidants, fluorescing agents, brightening agents, shine and gloss enhancers, softening agents, conditioning agents, water-repellants, and charge-modifiers (agents to modify the charge on the surface of a proteinaceous substrate for various purposes such as to make it attract chemical moieties of the opposite charge).

Residues $n_1$ and $n_2$ in Formulae (1) and (2) may be present in any order. The ratio of $n_1$ to $n_2$ is from about 1:99 to about 99:1; preferably from about and 5:95 to about 95:5, and more preferably from about 10:90 to about 90:10.

Residues $n_3$, $n_4$, and $n_5$ in Formulae (3) and (4) may be present in any order. The ratio of $n_3:n_4:n_5$ is from about 1:1:98 to about 45:45:10; preferably from about and 5:5:90 to about 45:45:10, and more preferably from about 10:10:80 to about 40:40:20.

The molecular weight of the polyimido compounds is a matter of preference subject to such factors as the particular type of polyimido compound used, the type and charge characteristics of the water-solubilizing/dispersing moiety employed, the proteinaceous substrate employed, the resulting properties desired, as well as the particular application for which the compound may be used. In general, for internal modifications of proteinaceous substrates, the molecular weight of the polyimido compound will be under about 5000 and the water-solubilizing/dispersing moiety will be neutral or amphoteric (with a net neutral charge). In general, for external modifications of proteinaceous substrates, the molecular weight of the polyimido compound may be under or over 5000. However, polyimido compounds having a molecular weight over 5000 and cationic water-solubilizing/dispersing moieties will tend to remain on the surface rather than penetrate the proteinaceous substrate. However, techniques such as swelling the proteinaceous substrate may be employed to internally modify the proteinaceous substrate with polyimido compounds of higher molecular weight. In one embodiment, the molecular weight of the polyimido compound in Formula (1) and (2) is from about 300 to about 5000, preferably from about 1000 to about 4000; more preferably from about 1000 to about 3000; and most preferably from about 1000 to about 2000. In another embodiment, the molecular weight of the polyimido compound in Formula (1) and (2) is from about 5000 to about 1,000,000, preferably from about 5000 to about 500,000; more preferably from about 5000 to about 100,000; and most preferably from about 5000 to about 50,000.

In one preferred embodiment, the polyimido compound is a polysuccinimide represented by Formula (1). In another preferred embodiment, the polyimido compound is a polyglutimide represented by Formula (2). In yet another preferred embodiment, the polyimido compound is a polysuccinimde represented by Formula (3). In yet another preferred embodiment, the polyimido compound is a polyglutimide represented by Formula (4). In still another preferred embodiment, the polyimido compound is a copolymer of the polysuccinimide represented by Formula (1) (before derivatization) with the polyglutimide represented by Formula (2) (before derivatization). In still another preferred embodiment, the polyimido compound is a copolymer of the polysuccinimide represented by Formula (3) (before derivatization) with the polyglutimide represented by Formula (4) (before derivatization).

The scope of the present invention need not be limited to polyimido compounds such as polysuccinimide compounds, polyglutimide compounds, and copolymers thereof, but may also include imido compounds. The imido compounds may be water-soluble or water-dispersible natural or synthetic polymers to which reactive imide moieties such as succinimide, glutimide, or phthalimide groups have been appended or, into the backbones of which, reactive imide moieties have been incorporated to form imido compounds. These imido compounds can be prepared by copolymerization reactions or by polymer modification reactions.

The nucleophilic catalytic agents in the two-part systems of the present invention are agents that have the ability to catalyze nucleophilic substitution of the carbonyl groups present in the polyimido compound by the nucleophilic groups present in the proteinaceous substrate. Nucleophilic catalytic agents are believed to function by a two-step mechanism (Advanced Organic Chemistry, Jerry March, John-Wiley & Sons, 1992, pp.330–335), wherein a nucleophilic catalytic agent first reacts with a carbonyl group (such as is present in the polyimido compound) to form a reactive intermediate, followed by displacement of the nucleophilic catalytic agent from the carbonyl group by a nucleophilic group (such as is present in the proteinaceous substrate). The nucleophilic catalytic agents in the two-part systems of the present invention may be selected from a wide variety of water-soluble/dispersible catalytic agents and mixtures of catalytic agents. Both organic and inorganic agents may be used provided the nucleophilic catalytic agent provides a catalytic effect. Nonlimiting illustrative specific examples of classes of nucleophilic catalytic agents may be selected from the group consisting of pyridines, tertiary amines, thiols, and peroxides. Preferably, the nucleophilic catalytic agents is selected from the group consisting of hydrogen peroxide (peroxide), dimethyl amino pyridine (pyridine), triethanolamine (tertiary amine), 1,4-diazabicyclo(2.2.2)octane (DABCO, tertiary amine), and 2-mercaptoethanol (thiol).

The amount of nucleophilic catalytic agent used in the present invention may vary depending upon the catalytic ability for the particular nucleophilic catalytic agent. In general, the amount of nucleophilic catalytic agent present is the amount required to obtain the desired result. In a preferred embodiment, the imide group of the polyimido compound and the nucleophilic catalytic agent are present in a molar ratio from about 1:0.01 to about 1:10, preferably in a molar ratio from about 1:0.1 to about 1:10, and more preferably in a molar ratio from about 1:1 to about 1:8.

The pH value of the aqueous solution of nucleophilic catalytic agent is such that when the aqueous nucleophilic catalytic agent is mixed with the polyimido compound, the resulting mixture will have a pH in a range sufficient to enable the nucleophilic catalytic agent to react with the polyimido compound, i.e., in a range in order to deprotonate a sufficient quantity of nucleophilic groups present on the nucleophilic catalytic agent which may then readily react with the carbonyl groups on the reactive polyimido compound. This pH value of the aqueous solution of nucleophilic catalytic agent is also in a range sufficient to enable the proteinaceous substrate to react with the complexed nucleophilic catalytic agent/polyimido compound in order to deprotonate nucleophilic groups (amino groups, alcohol groups, phenolic groups, sulfhydryl groups, and carboxyl groups) present on the proteinaceous substrate which may then readily react with the complexed nucleophilic catalytic agent/polyimido compound. In a preferred embodiment, the pH value of the aqueous solution of a nucleophilic catalytic agent is above about 6, more preferably above about 7, and most preferably 8–10.

The time sufficient to allow the polyimido compound to react with the proteinaceous substrate is subject to such factors as the particular type of polyimido compound used, the nucleophilic catalytic agent employed, the water-solubilizing/dispersing moiety employed, the proteinaceous substrate employed, the temperature of the application, the resulting properties desired, as well as the particular application for which the compound may be used. In general, the time sufficient to allow the polyimido compound to react with the proteinaceous substrate may range from seconds to an hour.

After reaction of a portion of the imide groups of the water-insoluble reactive polyimide, the water-soluble/dispersible polymer, together with the nucleophilic catalytic agent, can now act as an acylating agent which can be covalently and permanently bonded to various nucleophilic groups present on a proteinaceous substrate. The proteinaceous substrates which may be employed in the present invention include all substrates containing nucleophilic groups which can covalently react with the polyimido acylating compounds. Suitable nucleophilic groups include amino groups, alcohol groups, phenolic groups, sulfhydryl groups, and carboxyl groups. Preferred proteinaceous substrates may be selected from the group consisting of hair, wool, skin, leather, silk, fur, felt, and nails.

The polyimido acylating compounds and nucleophilic catalytic agents of the present invention may be employed in a pharmaceutically acceptable carrier to form therapeutic compositions. Suitable pharmaceutically acceptable carriers may be selected from the group consisting of water, water/alcohol mixtures, water/glycol mixtures, and mixtures thereof. Preferably, the pharmaceutically acceptable carrier is water.

The amount of polyimido compound present in the therapeutic compositions of the present invention is a therapeutically effective amount, that is, an amount effective to impart the modification properties desired. A therapeutically effective amount of polyimido compound is that amount of polyimido compound necessary for the inventive compound to provide the desired therapeutic effect. The exact amount of polyimido compound is a matter of preference subject to such factors as the particular type of polyimido compound, the molecular weight of the polyimido compound employed, the temperature of the application, the resulting properties desired, as well as the particular application for which the therapeutic composition may be used, i.e, substrate type, application, conditions, end-use. In a preferred embodiment, the polyimido compound in the pharmaceutically acceptable carrier is present in an amount from about 1% to about 70%, preferably from about 2% to about 60%, more preferably from about 3% to about 50%, and most preferably from about 5% to about 15%, by weight.

Many chemical modifications used to bleach, dye, or permanently wave hair also cleave the disulfide cross-linkages (from the amino acid cystine) which give the hair its strength. For example, it is known that disulfide bonds in hair are extensively cleaved as a result of exposure to the hydrogen peroxide used during the bleaching process. Not only does the hydrogen peroxide destroy the melanin in the hair resulting in a lighter color, but the hydrogen peroxide also weakens the hair by cleavage of the sulfur-sulfur cross-links. Dyeing of hair is also typically carried out by mixing the dye precursor (usually phenylenediamine/resorcinol) with a solution of hydrogen peroxide. The purpose of the hydrogen peroxide (or other bleaching agent) is two-fold, in that it destroys the melanin, thereby lightening the hair, and also catalyzes the formation of the dye itself. Some cleavage of disulfide cross-linkages can occur as a result of exposure to the hydrogen peroxide used in the dyeing formulation. The permanent waving process, which cleaves disulfide cross-linkages and forms new cross-links which lock the hair into the new array or style, also has the result of weakening the hair due to the failure of all of the sulfur-sulfur cross-links to reform.

Multifunctional Systems

As set out above, chemical damage done to hair by bleaching, permanent waving, or the like, can be repaired in accord with the present invention by treating the damaged hair with a water-soluble/dispersible polyimide to impart new cross-links into the hair fiber. Preferably, the polyimide has a molecular weight ranging from about 1000 to about 4500 and a net neutral charge. In a non-catalyzed system, a two-step process is required in which the bleaching, permanent waving, or dyeing process is first carried out, and then repair is achieved via exposure of the hair to the water-soluble polyimide. In a catalyzed system, repair can be carried out by the simultaneous regeneration of sulfur-sulfur cross-links as the bleaching, dyeing, or permanent waving process is carried out.

One Step Non-Degradative Hair Bleaching Process

A one-step process for the bleaching of hair that leaves the hair in a lightened, but non-weakened state can be achieved by the addition of an amount of a water-soluble/dispersible polyimide (preferably of Mw 1000 to 4500 and neutral in charge) sufficient to yield a final solution of from about 1% to about 10% actives (in the polyimide) to an effective amount of aqueous hydrogen peroxide (or other bleaching agent) in a buffered solution from pH 7 to pH 12. The solution is applied to the hair and allowed to remain in contact until the desired color is achieved.

One Step Non-Degradative Hair Dyeing Process

A one-step process for the dyeing of hair that leaves the hair in a colored, but non-weakened state can be achieved by the addition of an amount of a water-soluble/dispersible polyimide (preferably of Mw 1000 to 4500 and neutral in charge) sufficient to yield a final solution of from about 1% to about 10% actives (in the polyimide) to an effective amount of hydrogen peroxide (or other bleaching agent) and to an effective amount of a dye agent (e.g., phenylenediamine/resorcinol or to a water-soluble/dispersible polyimide functionalized with a dye moiety) in a buffered solution preferably from pH 7 to 12. The solution is applied to hair and allowed to remain in contact until the desired color is achieved.

One Step Non-Degradative Hair Permanent Waving Process

A one-step process for the permanent waving of hair that leaves the hair in a permanent waved, but non-weakened state can be achieved by the addition of an amount of a water-soluble/dispersible polyimide (preferably of Mw 1000 to 4500 and neutral in charge) sufficient to yield a final solution of from about 1% to 10% actives (in the polyimide) to an effective amount of an agent used for cleavage of cystine disulfide bonds in a buffered solution from preferably pH 7 to 12. The solution is applied to the hair and allowed to remain for such time as is required to achieve the desired level of set.

Accordingly, the two-part systems of the present invention, useful for treating proteinaceous substrates, may further comprise an agent also useful for treating proteinaceous substrates, including those agents used to bleach, dye, or permanently wave hair. Examples of other agents, useful for treating proteinaceous substrates, that may be employed with the two-part systems of the present invention include alkali sulfites, alkali bisulfites, hydrogen peroxide, organic peroxides, organic thiols, alkali salts of thioglycolic acid, and alkaline salts of thioglycolic acid.

In a specific embodiment, the present invention is directed to a method for treating a proteinaceous substrate which comprises the steps of:

(a) contacting a polyimido compound with an aqueous solution of an nucleophilic catalytic agent to form a mixture, wherein the pH value of the aqueous solution of nucleophilic catalytic agent is such that when the aqueous nucleophilic catalytic agent is mixed with the polyimido compound, the resulting mixture will have a pH in a range sufficient to enable the nucleophilic catalytic agent to react with the polyimido compound; and (b) contacting the mixture from step (a) with a proteinaceous substrate for a time sufficient to allow the mixture to react with the proteinaceous substrate;

wherein the polyimido compound is selected from the group consisting of polysuccinimide compounds represented by Formula (1):

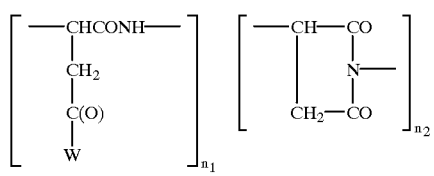

polyglutimide compounds represented by Formula (2);

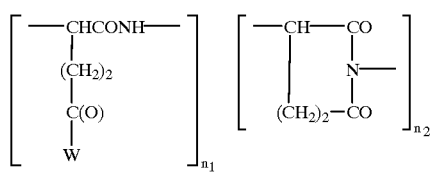

polysuccinimide compounds represented by Formula (3):

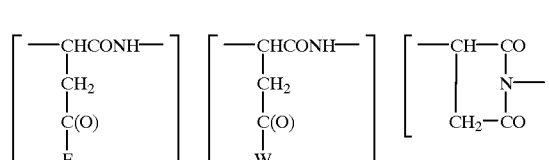

polyglutimide compounds represented by Formula (4);

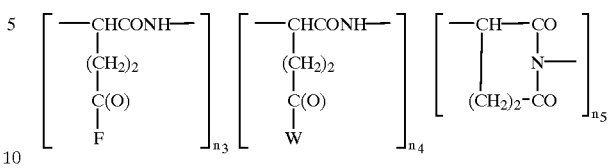

copolymers of the polysuccinimide compounds represented by Formula (1) with the polyglutimide compounds represented by Formula (2); and copolymers of the polysuccinimide compounds represented by Formula (3) with the polyglutimide compounds represented by Formula (4);

wherein W is a water-solubilizing/dispersing moiety that provides water-solubility and/or water-dispersibility to the polyimido compound; F is a functionalizing moiety that provides functionality to the polyimido compound; the ratio of $n_1$ to $n_2$ is from about 1:99 to about 99:1; the ratio of $n_3$:$n_4$:$n_5$ is from about 1:1:98 to about 45:45:10; and the molecular weight of the polyimido compound is from about 300 to about 1,000,000.

In another specific embodiment, the present invention is directed to a proteinaceous substrate, having a polyimido compound covalently bonded to a portion thereof, wherein the polyimido compound is derived from a residue selected from the group consisting of polysuccinimide compounds represented by Formula (1):

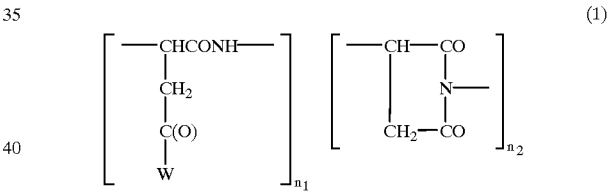

polyglutimide compounds represented by Formula (2);

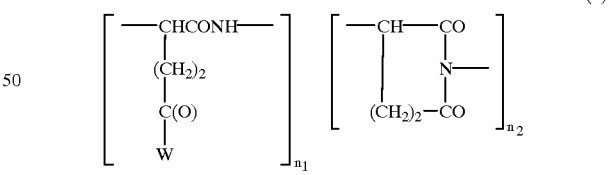

polysuccinimide compounds represented by Formula (3):

polyglutimide compounds represented by Formula (4);

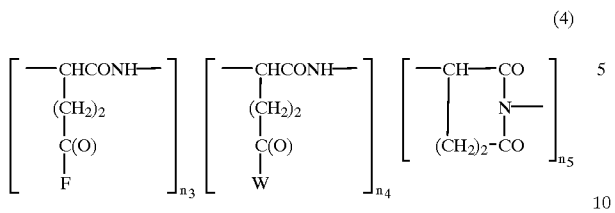

copolymers of the polysuccinimide compounds represented by Formula (1) with the polyglutimide compounds represented by Formula (2); and copolymers of the polysuccinimide compounds represented by Formula (3) with the polyglutimide compounds represented by Formula (4);

wherein W is a water-solubilizing/dispersing moiety that provides water-solubility and/or water-dispersibility to the polyimido compound; F is a functionalizing moiety that provides functionality to the polyimido compound;

the ratio of $n_1$ to $n_2$ is from about 1:99 to about 99:1; the ratio of $n_3:n_4:n_5$ is from about 1:1:98 to about 45:45:10; and the molecular weight of the polyimido compound is from about 300 to about 1,000,000.

In another specific embodiment, the present invention is directed to a method for treating a proteinaceous substrate which comprises the steps of:

(a) contacting an imido or polyimido compound with an aqueous solution of an nucleophilic catalytic agent to form a mixture, wherein the pH value of the aqueous solution of nucleophilic catalytic agent is such that when the aqueous nucleophilic catalytic agent is mixed with the imido or polyimido compound, the resulting mixture will have a pH in a range sufficient to enable the nucleophilic catalytic agent to react with the imido or polyimido compound; wherein the imido or polyimido compound has attached thereto a functionalizing moiety F that provides functionality to the imido or polyimido compound; and (b) contacting the mixture from step (a) with a proteinaceous substrate for a time sufficient to allow the mixture to react with the proteinaceous substrate.

In these latter three embodiments, suitable non-limiting proteinaceous substrates may be selected from the group consisting of hair, wool, skin, leather, silk, fur, felt, and nails. The polyimido compound may further be cross-linked to a multifunctional nucleophilic agent such as nucleophilic agents selected from the group consisting of 1,6-hexamethylenediamine, low-molecular weight polyethyleneimines, polyalkoxides, and polythiols. The water-solubilizing/dispersing moiety may further bear an ionic charge and be electrostatically bound to a moiety bearing the opposite charge such as those moieties selected from the group consisting of antimicrobials, ultraviolet chromophores, anionic dyes, anti-oxidants, fluorescing agents, brightening agents, shine and gloss enhancers, softening agents, and conditioning agents. In addition, the methods for treating a proteinaceous substrate may be carried out at elevated temperatures, such as from about 25° C. to about 55° C., to accelerate the reaction method.

In another specific embodiment, the present invention is directed to a composition useful for treating a proteinaceous substrate which comprises an aqueous mixture of a polyimido compound and a nucleophilic catalytic agent having a pH value in a range sufficient to enable the nucleophilic catalytic agent to react with the polyimido compound; wherein the polyimido compound is selected from the group consisting of polysuccinimide compounds represented by Formula (1):

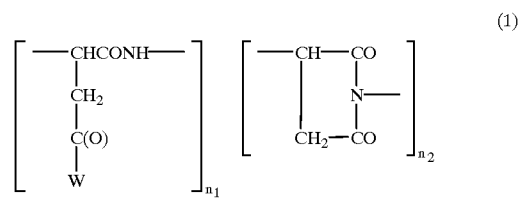

polyglutimide compounds represented by Formula (2);

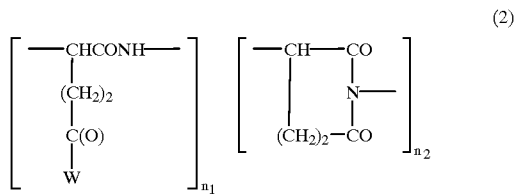

polysuccinimide compounds represented by Formula (3):

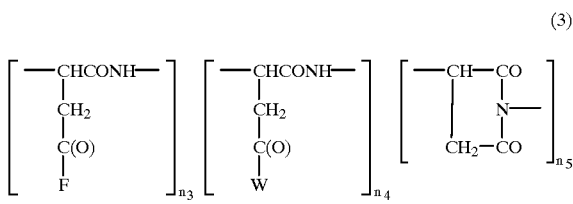

polyglutimide compounds represented by Formula (4);

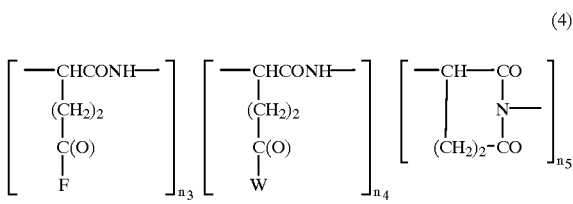

copolymers of the polysuccinimide compounds represented by Formula (1) with the polyglutimide compounds represented by Formula (2); and copolymers of the polysuccinimide compounds represented by Formula (3) with the polyglutimide compounds represented by Formula (4);

wherein W is a water-solubilizing/dispersing moiety that provides water-solubility and/or water-dispersibility to the polyimido compound; F is a functionalizing moiety that provides functionality to the polyimido compound; the ratio of $n_1$ to $n_2$ is from about 1:99 to about 99:1; the ratio of $n_3:n_4:n_5$ is from about 1:1:98 to about 45:45:10; and the molecular weight of the polyimido compound is from about 300 to about 1,000,000.

Use of the Water-solubleldispersible Polyimides Compounds for Modifying Hair

Hair may be reacted with a water-soluble/dispersible polyimide in order to impart a permanent benefit as set out below.

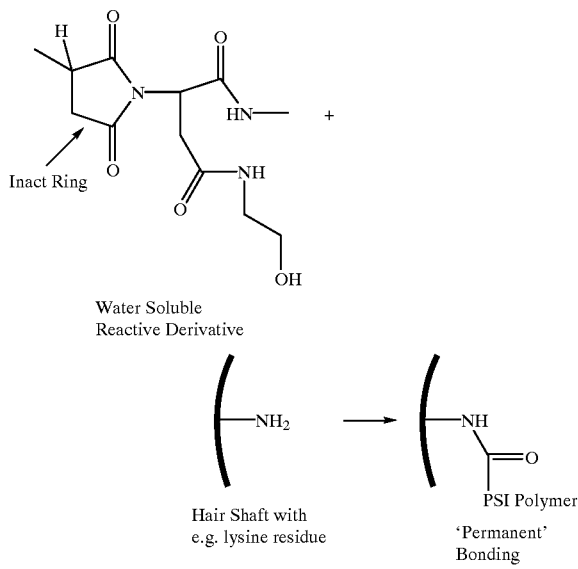

Water Soluble
Reactive Derivative

Hair Shaft with
e.g. lysine residue

PSI Polymer
'Permanent'
Bonding

Internal Modification of Hair with Water-soluble/dispersible Polyimides

Reparation of Chemically Damaged Hair

Perming and bleaching of hair results in cleavage of the sulfur-sulfur cross-linkages connecting the protein chains resulting in a weakening of the hair. In addition, the perming formulations are generally very alkaline and may also cleave some amide linkages in the protein chains resulting in a further weakening of the hair. This effect is especially pronounced when the hair is wet. This chemically damaged hair can be repaired by imparting to the hair additional cross-linkages through reaction of a multifunctional acylating agent of the present invention with the various nucleophilic groups present in the hair. Nucleophilic moieties, such as the free amino groups present in the basic amino acids lysine, arginine, or histidine (which are naturally present in hair), terminal amino groups resulting from cleavage of amide bonds, sulfhydryl groups from the cleavage of cystine, and phenolic groups present in aromatic amino acids may all be employed in the acylation reaction.

Post Cross-linking to Further Repair Chemically Damaged Hair

In addition to cross-linking the protein chains in the hair with the polyimide acylating agents set out above, multifunctional nucleophilic agents such as 1,6-hexamethylenediamine, low-molecular weight polyethyleneimines, polyalkoxides, and polythiols, can be added to the hair in order to react with the acylating agent and to promote the development of an internal polymeric network which can further strengthen the hair. Damaged hair may be treated with water-soluble/dispersible polyimides of various molecular weights ranging from 1000 to 4500, and preferably exhibiting a net neutral charge (due to the solubilizing group).

Non-Degradative Permanent Waving or Set

Perming or set can be imparted to hair without cleaving the disulfide bonds and without weakening of the hair by using a low molecular weight neutral charged water-soluble/dispersible polyimide to form new chemical cross-links between the polyimide and various nucleophiles (i.e., amino groups in lysine, terminal amino groups, phenoxide groups, etc). which exist within the hair fiber. Alternatively, additional cross-links can be formed to develop an internal polymeric structure by first allowing the polyimide to penetrate the hair and then following with the addition of multifunctional nucleophilic agents such as polyamines, polythiols, and the like. In one preferred embodiment, a water-soluble/dispersible polyimide of the present invention, having a molecular weight between approximately 300 and 5000, is applied to hair (which has been placed in a curled array) at a pH between about 4 and about 7 and allowed to penetrate the hair. After a time sufficient to penetrate the hair, the hair is treated with a buffer solution having a pH 8–10 and at a temperature between 20–55° C. In a more preferred embodiment, a water-soluble/dispersible polyimide, which is neutral in charge, and having a molecular weight between approximately 1000 and 4000 is used as above at a temperature between 30 and 55° C. In a most preferred embodiment, a water-soluble/dispersible polyimide, which is neutral in charge, and having a molecular weight between approximately 2000 and 3000 is used as above at a temperature between 35 and 45° C.

External Modification of Hair with Water-soluble/dispersible Polyimides

Reaction of a water-soluble/dispersible polyimide of the present invention can be confined to the exterior of the hair generally by controlling the molecular weight and the charge of the polyimide. A water-soluble/dispersible polysuccinimide of molecular weight>5000 can be applied to the hair at the appropriate pH, whereupon the pH is elevated, and the hair is heated to effect the covalent linkage with the polymer.

The Primer Approach

Intact hair is normally quite hydrophobic. However reaction of hair with a water-soluble/dispersible polyimide, especially one which is highly charged or in which the polymer will exhibit a charge after hydrolysis of residual imide moieties, will result in hair which has a much more hydrophilic surface. Hair normally has an overall negative charge because of the presence of high levels of aspartic acid and glutamic acid. Reaction of hair with a polyimide made water-soluble/dispersible by the presence of a large number of quaternary groups will impart an overall positive charge on the surface of the hair. An advantage of covalently binding a water-soluble/dispersible polyimide carrying a high positive charge to hair is that the positive charges on the polymer become a magnet for anionic species. By priming the hair with a positively charged polymer, such as the structure shown below, one can attract and bind anionic chemical moieties:

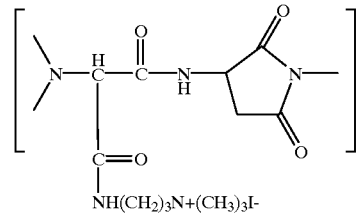

The primer approach may be used to impart a wide variety of beneficial properties to the hair by exposing the cationically modified hair to the appropriate anionic group (typically delivered from a shampoo, lotion, spray etc.), which would then become electrostatically bound to the polymer. The following are potential uses of this approach (a) Antimicrobials having an anionic charge, e.g., Triclosan, a phenolic can be bound to the surface of hair providing protection to the hair and the scalp from attack by microrganisms.

(b) UV chromophores, having anionic charge such as methoxycinnamic acid or para-aminobenzoic acid, can be bound to hair providing protection to the hair from UV light.

(c) Anionic dyes, such as tartrazine, can be bound to hair to provide color.
(d) Anti-oxidants, such as sodium ascorbate, can be bound to hair providing protection from oxidation to the hair and to its melanin.
(e) Fluorescing agents.
(f) Brightening agents.
(g) Shine and gloss enhancers.
(h) Softening agents.
(i) Conditioning agents.

Use of the Primer Approach to Impart Conditioning to Hair

Damaged hair, whether it is chemically damaged from a bleaching or perming process, from weathering, or from physical damage such as teasing or ratting, typically has very poor combing properties. A number of positively charged water-soluble/dispersible polyimides may be reacted onto the surface of damaged hair to attract conditioners. Ease of wet combing is viewed as an indication of "conditioned hair". Results from experiments (described below) testing this idea clearly show that the highly positively charged polyimide having been covalently reacted to the hair, is then able to electrostatically bind the sodium lauryl sulfate, in which it is subsequently washed, to itself and in the process to the surface of the hair where it serves to lubricate the hair and to provide improved wet combing.

Use of the Water-soluble/dispersible Polyimido Compounds for Modifying Skin

In principal, the same approach used to achieve external modification of hair can be used to modify the surface of the skin, i.e., either high molecular weight>5000 or positively charged water-soluble/dispersible polyimides would be used. The polyimide would be applied to the skin at a pH between 4 and 7, whereupon the pH of the skin would then be raised with a buffer to above about 7 and the temperature raised to between 35 and 45°C.

Use of the Water-soluble/dispersible Polyimido Compounds in Skin Care

The water-soluble/dispersible polyimido compounds of the present invention may be employed to protect skin from alkaline attack, such as from dishwashing liquids. A water-soluble/dispersible polyimido compound, such as the structure set out below or others in which the the solubilizing groups are present at a minimum concentration so that hydrolysis of the residual succinimide moieties would result in the maximum amount of aspartate residues present, may be employed to bind to the skin and exhibit maximum buffer capacity.

Use of the Primer Approach to Provide Benefit to Skin

As set out above for hair, a water-soluble/dispersible polyimide containing high levels of cationicity, such as is shown below, may be covalently bound to skin.

By using the primer approach, a wide variety of anionic species may be bound to the skin to provide numerous benefits. Anti-microbials and anti-fungals containing anionic groups would electrostatically bind to the positively charged primer and gradually release to the skin thereby giving longer lasting protection from various microorganisms. Ultra-violet chromophores, such as salts of methoxycinnamic acid and n, n- dimethylamino p-benzoic acid would bind thereby giving increased sun protection. Anionic Dyes could be applied to the skin treated with the positively charged polyimide thus providing body art having semi-permanence. Anionic conditioning agents, e.g., anionic silicones or salts of fatty acids, or sulfated hydrocarbons could be electrostatically bound to impart to the skin a conditioned feel. Reparative or rejuvenative agents such as salts of glycolic acid or hyaluronic acid could be bound to the skin and then gradually released over time.

Hair Dyeing

In Formula (1) and (2), F may be a dye moiety such as one or more of the 3 primary colors shown below. Polyimides containing a dye moiety as the functionalizing moiety may be used to covalently bind the dye to the hair and impart permanent color to it.

Skin Dyeing and Tanning

The approach set out above for dyeing hair could also be used to apply semi-permanent body art (tattoos) to the skin as well as to tint the skin and to give it a tanned appearance.

Conditioning of Hair and Skin

The polyimides may have F moieties suitable for use as hair and skin conditioners. For example, F may be selected from the group consisting of part of an amide linkage derived from a long chain, branched or unbranched primary or secondary amine of between 6 and 50 carbon atoms; (2) part of an amide linkage derived from an aminopolysaccharide containing from 1 to 1 million repeating units; (3) part of an amide linkage derived from an aminosilicone; and (4) part of an ester linkage derived from a branched or unbranched alcohol of from 6 to 50 carbons.

Ultraviolet Protection of Hair and Skin

When hair is exposed to ultraviolet radiation, the result is a weakening of the hair fiber (caused by cleavage of the disulfide bonds) as well as an overall dulling and loss of shine. In cases where the hair is artificially colored, the wavelength of the light transmitted by the dye may be shifted higher or lower and thus the color of the hair will be affected. Additionally, melanin, which gives hair its natural color, may be destroyed by excessive ultraviolet radiation.

Exposure of skin to ultraviolet light results in a reddening of the skin or erythema (depending on the wavelength of light used), the development of facial lines, and in cases of long term exposure, cancerous lesions.

If F is an ultraviolet chromophore, as set out below, absorbing over the appropriate range, then the polyimide with the ultraviolet chromophore when covalently bound can be used to impart long lasting protection to the hair and skin. An example of a functionalized water-soluble/dispersible ultraviolet protecting polyimide is shown below.

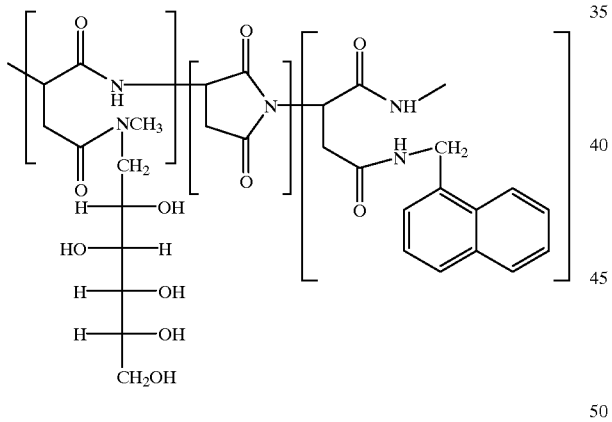

UV max 280, molar absorptivity 8120L/(mol cm)

Other UV chromophores which may be employed include but are not limited to the following:

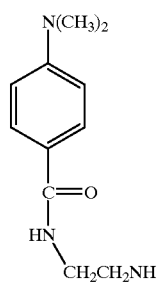

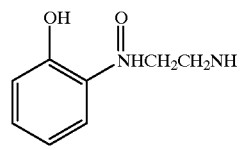

Protection of Hair and Skin from Oxidation

Oxidative forces can damage hair and skin in a variety of ways, e.g., by destroying sulfur-sulfur cross-links, by modifying the structure of various hair dyes, and by oxidation of other amino acids. By using the reactive polymer to deliver and covalently bind an anti-oxidant to the hair or skin, these substrates can be protected against this source of damage. An example of an anti-oxidant and a polyimide containing the antioxidant is set out below.

Anti-microbial Protection

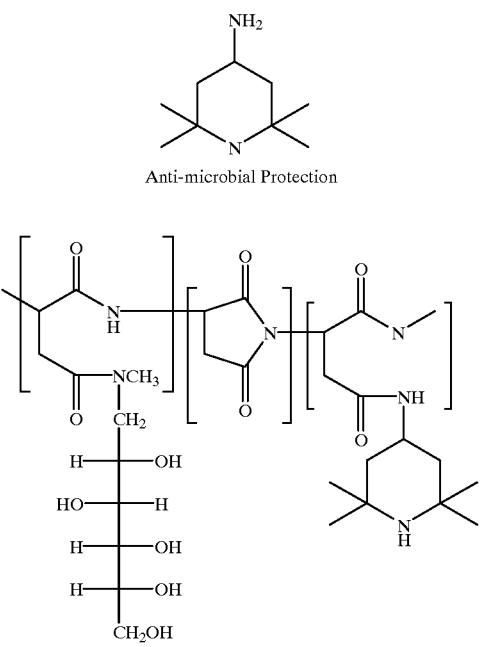

It is well known that quaternary ammonium salts display anti-microbial properties, particularly those with carbon chain lengths between 12 and 18 carbon atoms. Quaternized polyaspartate salts in which the hydrophobic chain was varied from 12 to 18 carbon atoms were also found to display excellent anti-microbial activity. Thus a series of structures of the type shown below in which the hydrophobe is varied between 12 and 18 carbons could be employed to display good anti-microbial properties when covalently bound to skin and hair.

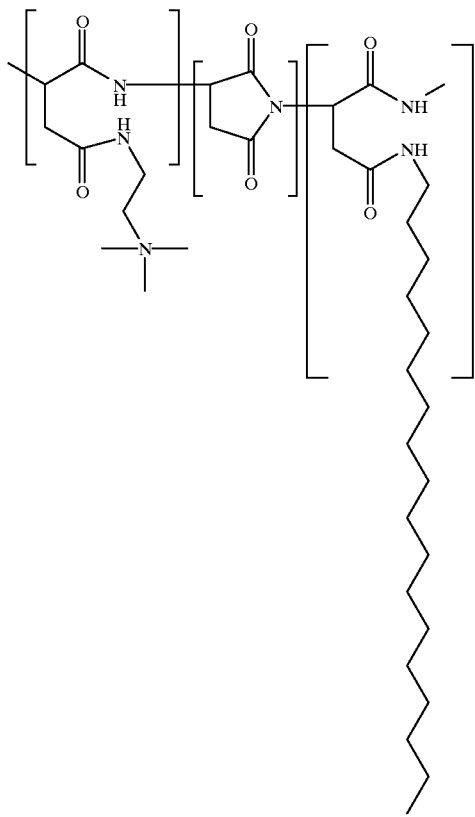

Improvement in Gloss and Luster

Functional groups having gloss and luster enhancing properties (e.g. silicones, optical brighteners, etc.) may also be bound to hair to yield long lasting improvement in gloss and luster.

Water-Repellency

A number of chemical groups (e.g. silicones, hydrofluorocarbons, etc.) impart water repellency to various substrates. Reacting these water repellant functionalizing groups with the succinimide groups of the water-insoluble polysuccinimide would result in the formation of a water-soluble/dispersible reactive derivative which upon reaction would result in the surface of the hair or skin having long lasting water repellent capabilities.

Fluorescence of Skin and Hair

Reacting fluorescing functionalizing groups with the succinimide groups of the water-insoluble polysuccinimide would result in the formation of a water-soluble/dispersible reactive derivative which upon reaction would result in the surface of the hair or skin having long lasting fluorescing capabilities.

Multiple Benefits

The functionalized polyimides of the present invention may also impart more than one benefit by preparing a polyimide having more than one type of F group (e.g., a polyimide with both coloring and ultraviolet protection). The water-solubilizing group itself may also carry additional functionality through the primer approach. Thus, in the structure below, a conditioning polymer may be first covalently bound to the hair, followed by treatment with an anionic dye which binds to the quaternary functionality of the polymer, resulting in a long lasting red color being imparted to the hair.

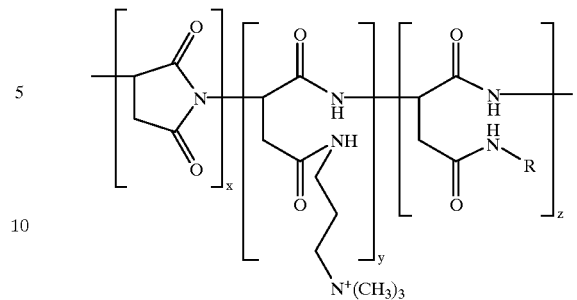

Water-soluble/dispersible functionalized derivative of polysuccinimide where x=40 mole %, y=50 mole %, z=10 mole %, and where R=lauryl amine.

The precise formulation of the therapeutic composition will vary depending upon the specific end use. Other ingredients may also be incorporated into the therapeutic compositions as dictated by the nature of the desired composition as well known by those having ordinary skill in the art. The therapeutic compositions are readily prepared using methods generally known in the therapeutic arts. Examples of additives traditionally used in therapeutics include emollients, rheology modifiers, fillers, humectants, thickeners, preservatives, dyes, and pigments, which may be employed in conventional amounts.

Illustrative examples of emollients include isopropyl myristate, isopropyl palmitate, isopropyl laurate, isopropyl stearate, glyceryl stearate, dioctyl adipate, cetyl oleate, PEG-7 glyceryl cocoate, PEG-15 glyceryl trioleate, polyglyceryl-3 dicaprate, polyglyceryl-3 laurate, cyclomethicone, and PPG-1-ceteth-1. Emollients are generally used in amounts from 2 to 30 parts by weight, preferably 3 to 20 parts.

Illustrative examples of thickeners include carbomer, carrageenan, salts of alginic acid, derivatives of chitosan, bentonite, casein, fumed silica, guar gum, gum tragacanth, hydroxy-ethylcellulose, locust bean gum, methylcellulose, polyacrylic acid salts (ammonium, potassium, sodium), polyvinyl alcohol, sodium carboxymethyl cellulose, and starches. When present, thickeners will be used in amounts up to about 10 parts by weight.

Illustrative examples of fillers include bentonites, calcium carbonate, calcium silicate, clay, mica, nut shell flours, silica, talc, uncooked starches, and wood flour. When present, fillers will be used in amounts up to about 20 parts by weight.

Illustrative examples of humectants include glucamine, PCA, glucuronic acid, polyglycerin-4, diethylene glycol, glycerine, hexylene glycol, propylene glycol, sorbitol, sucrose, and urea. When present, humectants will be used in amounts up to about 10 parts by weight.

Surfactants are often employed in therapeutic compositions to increase the penetrating effects of the therapeutic. The surfactants may be one or more of anionic, cationic, amphoteric or nonionic surface-active compounds. Suitable anionic emulsifiers are, for example, alkyl sulfonates, alkylaryl sulfonates, alkyl sulfates, sulfates of hydroxylalkanols, alkyl and alkylaryl disulfonates, sulfonated fatty acids, sulfates and phosphates of polyethyoxylated alkanols and alkylphenols, as well as esters of sulfosuccinic acid. Suitable cationic emulsifiers are, for example, alkyl quaternary ammonium salts, and alkyl quaternary phosphonium salts. One type of suitable non-ionic emulsifier is the addition product of 5 to 50 moles of ethylene oxide adducted to straight-chain and branched-chain alkanols with 6 to 22 carbon atoms, or to alkylphenols, higher fatty acids, higher fatty acid amines, or primary and secondary higher alkyl amines. Other suitable non-ionic emulsifiers are one or more block copolymers of propylene oxide with ethylene oxide. Preferred surfactants include fluorinated alkyl amphoterics or sodium dioctylsulfosuccinate. When present, the surfactant will be used in amounts of about 0.05 to 5.0 parts by weight.

One skilled in the art, having the knowledge of the present specification, will readily ascertain those applications in which the use of the inventive therapeutic compositions would be advantageous. Any conventional method of applying the therapeutics to the particular substrates may be employed. These methods are well known in the field of therapeutics.

Throughout this application, various publications have been referenced. The disclosures in these publications are incorporated herein by reference in order to describe more fully the state of the art.

Throughout this disclosure, applicant will suggest various theories or mechanisms by which applicant believe the components in the therapeutic compositions function together in an unexpected manner to provide unique treatments for proteinaceous substrates such as skin and hair. While applicant may offer various mechanisms to explain the present invention, applicant does not wish to be bound by theory. These theories are suggested to better understand the present invention but are not intended to limit the effective scope of the claims.

The present invention is further illustrated by the following examples which are presented for purposes of demonstrating, but not limiting, the preparation of the compounds and compositions of this invention.

EXAMPLES

The following examples describe the use of catalyzed water-soluble/dispersible reactive functionalized derivatives of polyimido compounds useful for modifying proteinaceous substrates in accord with the present invention.

Example 1

Coloration of Hair

This example demonstrates the ability to color hair in a manner that is resistant to washout by employing the dye functionalized poly(succinimide) compounds, and the methods of applying them, in accord with the present invention.

The polymers used to demonstrate the present method both have the general structure set out below.

Structure #1
General Structure of Functional Reactive Polymer

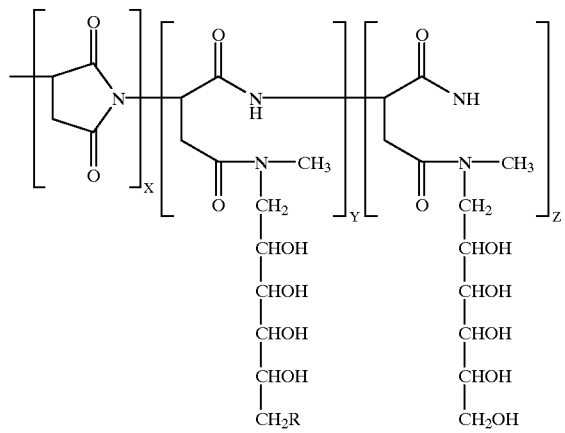

Wherein X, Y, and Z represent approximately 50 mole %, 20 mole %, and 30 mole %, respectively, and R denotes the moiety having a visible absorbance (dye) (note that this is an approximate structure because the exact number and position of R units per Y repeat unit is unknown).

In order to achieve a red polymer dye, the R unit is the following moiety where the R represents the point of attachment to the polymer:

Structure #2
Red Moiety

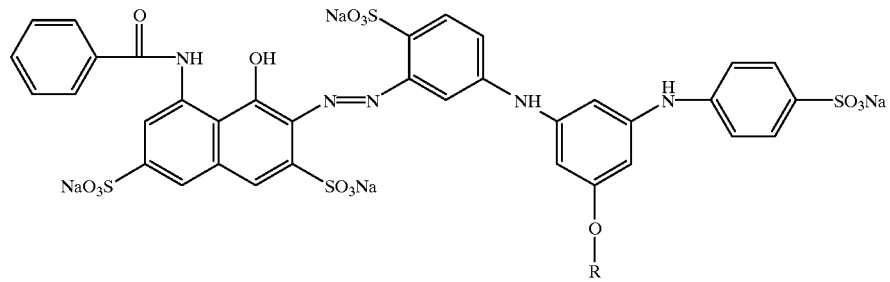

In order to achieve a blue polymer dye, the R unit is the following moiety where the R represents the point of attachment to the polymer:

Structure #3
Blue Moiety

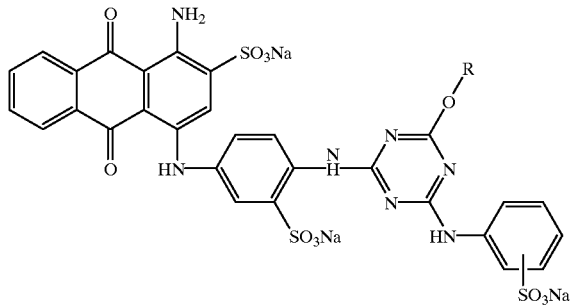

The following solutions were prepared using a polymer according to structure #1 where the color moiety is either structure #2 (red) or structure #3 (blue). A non-reactive polymer differs from Structure #1 in that the 'x' units are in the hydrated form of aspartic acid.

Process 1) 6% (mass) blue polymer in the following aqueous solution: 0.025molal sodium carbonate, 0.025molal sodium bicarbonate (pH=10).

Process 2) 6% (mass) blue polymer in the following aqueous solution: 3% (mass) hydrogen peroxide (pH =6.0).

Process 3) 6% (mass) blue polymer in the following aqueous solution: 3% (mass) hydrogen peroxide, 0.025molal sodium carbonate, 0.025molal sodium bicarbonate (pH=10).

Process 4) 6% (mass) blue non-reactive polymer in the following aqueous solution: 3% (mass) hydrogen peroxide, 0.025 molal sodium carbonate, 0.025 molal sodium bicarbonate (pH=10).

Process 5) 6% (mass) red polymer in the following solution: 3% (mass) hydrogen peroxide, 0.025 molal sodium carbonate, 0.025 molal sodium bicarbonate (pH=10).

Process 6) 6% (mass) red non-reactive polymer in the following aqueous solution: (mass) hydrogen peroxide, 0.025 molal sodium carbonate, 0.025 molal sodium bicarbonate (pH=10).

Process 7) 6% (mass) red polymer in the following solution: 3% (mass) hydrogen peroxide (pH=4.6).

Process 8) 6% (mass) red polymer in the following solution: 0.025 molal sodium carbonate, 0.025 molal sodium bicarbonate (pH=10).

Process 9) In addition to these experiments; the polymer was applied to hair according to a multi-step process. A 6% (mass) aqueous solution of the blue polymer was prepared. Hair was soaked in this solution for twenty minutes. The treated hair was then transferred to a pH=10 buffer solution for 20 minutes at 50° C.

Description of Experimental Procedure

Three ml aliquots of each of the solutions (Processes 1)–8)) were applied to ~2.5 grams/12 inch tresses of bleached/permed human hair. It was massaged into the hair fibers by mechanical rubbing. The treated tresses were allowed to stand at room temperature (approximately 22° C.) for 20 minutes. Each tress was rinsed thoroughly under running tap water. One of the three tresses was washed one time. One of the tresses was washed 5 times. The final tress was washed 20 times. Washing consisted of dipping the hair tress into approximately 100 ml of 10% (mass) sodium lauryl sulfate solution for 15 seconds and mechanically rubbing the hair tress from root to tip one time and rinsing thoroughly under running tap water. The results are described below by a comment on the relative intensity of coloration of each hair tress as a function of washing.

| | Results Description of Results | | |
|---|---|---|---|
| Process | 1 Wash | 5 Wash | 20 Wash |
| Process 1) | Dark Blue | Light Blue | Very Light Blue |
| Process 2) | Dark Blue | Light Blue | Very Light Blue |
| Process 3) | Dark Blue | Dark Blue | Dark Blue |
| Process 4) | Dark Blue | Light Blue | Very Light Blue |
| Process 5) | Red | Red | Red |
| Process 6) | Red | — | Pink |
| Process 7) | Red | Pink | Light Pink |
| Process 8) | Red | Pink | Light Pink |
| Process 9) | Dark Blue | Dark Blue | Dark Blue |

Discussion

The relative intensity varies from most intense to least intense as follows: Dark Blue, Light Blue, Very Light Blue and Dark Red, Red, Pink, and light Pink. The persistence of color over the course of 1, 5, and 20 washes indicates a successful treatment.

These results suggest the following conclusions. First, comparison of the results of Process 3) and 4) and Process 5) and 6) demonstrate the need for the polymer to have reactive imide groups in order to achieve a color that does not change during washing. Second, comparison of the results of Processes 1) and 2) to Process 3) and Process 7) and 8) to Process 6) demonstrates that both peroxide and elevated pH are necessary to promote a successful treatment. Finally, comparison of the results of Process 3) and Process 9) demonstrate that the one-step method of the present invention yields identical results to a multi-step process.

Example 2

Improvements in Wet Combability of Hair

This example demonstrates that the wet combability of hair can be improved by treatment with cationic poly (succinimide) compounds applied by the method of the present invention.

We have demonstrated (using a multi-step process) that a polymer with a structure given below is capable of improving the wet combability of hair when treated with an anionic species such as an anionic surfactant. It has been proposed that the polymer covalently binds to hair via the imide units and the cationic units attract and bind anionic species from solution to improve the condition of hair.

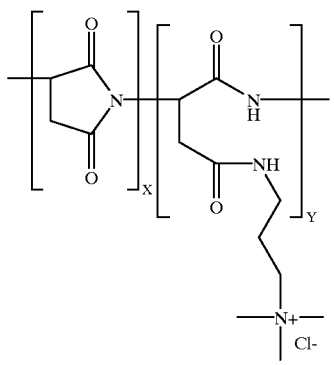

In this experiment, a polymer with the general structure given above where x and y are approximately 50% (mole) each and the weight average molecular weight of the starting poly(succinimide) is approximately 4,500 was applied to hair using both the two step process and the process of the current invention.

Experiment #1

A 10% (mass) aqueous solution of the polymer was prepared. Ten milliliter aliquots of each of the solution were applied to ~2.5 grams/12 inch tresses of bleached/permed hair. It was massaged into the hair fibers by mechanical rubbing. The treated tresses were allowed to stand at room temperature for 20 minutes. Ten milliliters of a buffered solution (0.025 molal/sodium carbonate/sodium bicarbonate, pH=10) were massaged into the hair tresses and hung in a 45° C. oven for 40 minutes.

Experiment #2

A 10% (mass) solution of the polymer was prepared in a solution of 3% (mass) hydrogen peroxide, 0.025 molal sodium carbonate/sodium bicarbonate. Three milliliter aliquots of the solution were applied to ~2.5 grams/12 inch tresses of bleached/permed hair. It was massaged into the hair fibers by mechanical rubbing. The treated tresses were allowed to stand at room temperature for 20 minutes.

After application of the polymer to hair each hair tress was washed 5, 10, 15, and 20 times in a solution of sodium lauryl sulfate (10% (mass)aq). Washing consists of dipping the hair tress in 100 ml of surfactant solution for 30 seconds followed by two rinses with water. A rinse consists of dipping the hair tress in 100 ml of water for 30 seconds.

An objective wet combability test was used to measure the work of wet comb and thus condition of the initial hair (0 washes), after treatment and 5 washes, 10 washes, 15 washes, and 20 washes. The results of the two experiments are tabulated below where the % of original work of wet comb is calculated by dividing the wet comb measurement by the initial (0 washes) value and multiplying by 100. Thus a lower percentage corresponds to an improvement in condition.

| | Results Description of Results | |
|---|---|---|
| | #1 | #2 |
| Initial | 100% | 100% |
| 5 Wash | 48 | 40 |
| 10 Wash | 50 | 43 |
| 15 Wash | 40 | 55 |
| 20 Wash | 39 | 45 |

As can be seen by the results, the one-step method of the present invention gives a similar improvement in the condition of hair as the two-step process.

Example 3

Dual Benefits (Color and Conditioning)

Multiple benefits may be imparted to various proteinaceous substrates employing the process for applying the water-soluble/dispersible polyimides of the present invention. For example, more than one functionalizing group F can be attached to the polymer or cationic groups on the polymer can be used to attract and bind beneficial species from solution. In this example, a polymer according to the structure given below is applied to hair and both a persistent coloration and an improvement in the wet combability is observed up to at least twenty washes in 10% sodium lauryl sulfate solution

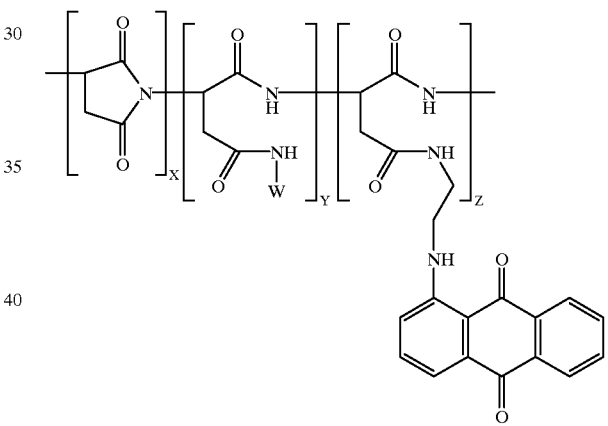

W is trimethyl propyl chloride; x, y, and z are the approximate mole % and are 60%, 30%, and 10% respectively. The weight average molecular weight of the starting polysuccinimde is approximately 30,000.

Description of Experiment

A 10% (mass) solution of the polymer was prepared in a solution of 3% (mass) hydrogen peroxide, 0.025 molal sodium carbonate/sodium bicarbonate. Three milliliter aliquots of the solution were applied to ~2.5 grams/12 inch tresses of bleached/permed hair. It was massaged into the hair fibers by mechanical rubbing. The treated tresses were allowed to stand at room temperature for 20 minutes.

After application of the polymer to hair each hair tress was washed 5, 10, 15, and 20 times in a solution of sodium lauryl sulfate (10% (mass)aq). Washing consists of dipping the hair tress in 100 ml of surfactant solution for 30 seconds followed by two rinses with water. A rinse consists of dipping the hair tress in 100 ml of water for 30 seconds.

An objective wet combability test (as described in example #2) was used to measure the work of wet comb and thus condition of the initial hair (0 washes), after treatment and 5 washes, 10 washes, 15 washes, and 20 washes. The results of the two experiments are tabulated below where the % of original work of wet comb is calculated by dividing the wet comb measurement by the initial (0 washes) value and multiplying by 100. Thus a lower percentage corresponds to an improvement in condition.

The initial color of the hair which was bleached and permed was yellow. The polymer provides a red/orange color.

| Results | | | | | |
|---|---|---|---|---|---|
| | Initial | 5 Wash | 10 Wash | 15 Wash | 20 Wash |
| % of Original Work of Wet Comb | 100% | 41% | 53% | 38% | 40% |
| Color | Yellow | Red/Orange | Red/Orange | Red/Orange | Red/Orange |

The results demonstrate that the polymer can both simultaneously color hair and improve its condition in a fashion that is resistant to washout with anionic surfactant.

Example 4

Nucleophilic Catalytic Agent

This example demonstrates the types of chemical compounds that are suitable to function as nucleophilic catalytic agents.

The following solutions were prepared using a polymer conforming approximately to structure #1 where the color moiety (R) is structure #3 (a blue dye chromophore). The molal concentration of the nucleophilic catalyst is identical to that of 3% peroxide used in example #1.

Process 1) 6% (mass) blue polymer in the following aqueous solution 0.025 molal sodium carbonate, 0.025 molal sodium bicarbonate, 0.87 molal dimethyl amino pyridine pH=10.2.

Process 2) 6% (mass) blue polymer in the following aqueous solution 0.87 molal sodium sulfite pH=7.8.

Process 3) 6% (mass) blue polymer in the following aqueous solution 0.87 molal sodium sulfite pH =10.8 (adjusted to pH with sodium hydroxide).

Process 4) 6% (mass) blue reactive polymer in the following aqueous solution : 0.87 molal 2 mercaptoethanol pH=9.8 (adjusted to pH with sodium hydroxide).

Process 5) 6% (mass) blue reactive polymer in the following aqueous solution 0.87 molal sodium thiosulfate pH=10.1 (adjusted to pH with sodium hydroxide).

Process 6) 6% (mass) blue reactive polymer in the following aqueous solution. 0.87 molal 1,4diazabicyclo (2.2.2) octane (DABCO) pH=9.8

Process 7) 6% (mass) blue reactive polymer in the following aqueous solution: 0.87 molal triethanolamine pH=10.6 (adjusted to pH with sodium hydroxide).

Description of Experimental Procedure

Three ml aliquots of each of these solutions were applied to ~2.5 grams/12 inch tresses of bleached/permed human hair. It was massaged into the hair fibers by mechanical rubbing. The treated tresses were allowed to stand at room temperature (approximately 22° C.) for 20 minutes. Each tress was rinsed thoroughly under running tap water. One of the tresses was washed one time. One of the tresses was washed 20 times. The results are described below by a comment on the relative intensity of coloration of each hair tress as a function of washing.

| Results Results of Nucleophilic Catalytic Agents | | | |
|---|---|---|---|
| | pH | 1 Wash | 20 Wash |
| Dimethyl Amino Pyridine | 10.2 | Dark Blue | Dark Blue |
| Sodium Sulfite | 7.8 | Light Blue | Light Blue |
| Sodium Sulfite | 10.8 | Light Blue | Light Blue |
| 2 Mercaptoethanol | 9.8 | Dark Blue | Dark Blue |
| Sodium Thiosulfate | 10.1 | Dark Blue | Light Blue |
| Triethanolamine | 10.6 | Blue/Dark Blue | Blue/Dark Blue |
| DABCO | 9.8 | Blue | Blue |

The addition of dimethyl amino pyridine, 2 mercaptoethanol, DABCO, or triethanolamine gives blue coloration on hair that is significantly more intense and persistent then a treatment where those reagents are absent. These data demonstrate that dimethyl amino pyridine, 2 mercaptoethanol, DABCO, and triethanolamine are capable of accelerating the modification of hair.

The addition sodium sulfite or sodium thiosulfate does not give blue coloration that is significantly more intense and persistent then a treatment where those reagents are absent. These data demonstrate that sodium sulfite and sodium thiosulfate are not capable of accelerating the modification of hair.

These data suggest that the nucleophilic catalytic agent can be selected from the general classes of compounds including: pyridines, tertiary amines, thiols, and peroxides.

Example 5

Definition of Process Variables

In this example, the relevant process variables are defined. Each variable is described individually below.

Time

In order to determine the impact of treatment time, the solution described above as Process 5) was prepared and three additional experiments were performed. In each case the polymer was applied to one tress of hair as described above. However, the treated hair tress was allowed to stand at room temperature for the following times: 5 minutes, 10 minutes, and 40 minutes. The tresses were then washed 20 times. The results are described by a comment on the relative intensity of coloration of each hair tress after washing.

| Time | |
|---|---|
| Time (minutes) | 20 Wash |
| 5 | Pink |
| 10 | Pink |
| 20 | Red |
| 40 | Red |

It appears that the color intensity is dependent upon time of treatment with most intense color occurring between 10 and 20 minutes. There appears to be no intensity advantage to times longer then 20 minutes.

Polymer Concentration

In order to determine the impact of polymer concentration, aqueous solutions of the red reactive polymer were prepared at 1%, 3%, 6%, and 10% (mass) in 3% (mass) hydrogen peroxide, 0.025 molal sodium carbonate, 0.025 molal sodium bicarbonate. The solutions were applied to hair as described above and were allowed to stand at room temperature for 40 minutes. The tresses were then washed 20 times. The results are described below by a comment on the relative intensity of coloration of each hair tress after washing.

| Polymer Concentration | |
| --- | --- |
| Concentration (mass %) | 20 Wash |
| 1 | Pink |
| 3 | Pink |
| 6 | Red |
| 10 | Dark Red |

As can be seen in the Table above, the color intensity is dependent upon polymer concentration.

pH

In order to determine the impact of pH, aqueous solutions of the red reactive polymer were prepared at 6% (mass) in 3% (mass) hydrogen peroxide at pH: 4.6, 7, 8, and 10. The solutions were applied to hair as described above and were allowed to stand at room temperature for 20 minutes. The tresses were washed 1, 5, and 20 times. The results are described below by a comment on the relative intensity of coloration of each hair tress as a function of washing. These data suggest that the lower limit to the pH range is greater than 4.6 but less than 7. The upper limit is in excess of pH=10.

| | pH | | |
| --- | --- | --- | --- |
| pH | 1 Wash | 5 Wash | 20 Wash |
| 4.6 | Red | Pink | Light Pink |
| 7 | Red | Red | Red |
| 8 | Red | Red | Red |
| 10 | Red | Red | Red |

Nucleophilic Catalytic Agent Concentration

In order to determine the impact of nucleophilic catalytic agent concentration on the process, aqueous solutions of blue reactive polymer were prepared at constant polymer content (6% (mass)), constant pH (pH=10), and the following hydrogen peroxide concentration (mass %): 0%, 1%, 3%, and 10%.

The solutions were applied to hair as described above and were allowed to stand at room temperature for 20 minutes. Tresses were washed 1, 5, and 20 times. The results are described below by a comment on the relative intensity of coloration of each hair tress as a function of washing.

| Nucleophilic Catalytic Agent Concentration | | | |
| --- | --- | --- | --- |
| Concentration (mass %) | 1 Wash | 5 Wash | 20 Wash |
| 0 | Dark Blue | Light Blue | Very Light Blue |
| 1 | Dark Blue | Dark Blue | Dark Blue |
| 3 | Dark Blue | Dark Blue | Dark Blue |
| 10 | Dark Blue | Light Blue | Light Blue |

These results demonstrate that the process is dependent on hydrogen peroxide concentration of the treatment solution. Those solutions containing between 0 and 1% and less than 10% gave successful treatments.

Example 6

While the data in these experiments demonstrates the applicability of the present invention for modifying hair, other nucleophilic sites on other proteinaceous substrates may also undergo the same acylation chemistry. Thus for example, hair, wool, skin, leather, silk, fur, felt, and nails, which all have nucleophilic sites available either along the polypeptide backbone or on the amino terminus, would be expected to react with the water-soluble/dipersible reactive succinimide functionality. The relative concentrations of the basic amino acids (lysine, histidine, and arginine) those most likely to undergo acylation) found in hair, wool, silk, leather, skin, and nails, are set out below.

| Amino Acid | Hair | Wool | Silk | Leather | Skin | Nails |
| --- | --- | --- | --- | --- | --- | --- |
| Lysine | 2.6–3.1 | 2.7 | 0.7 | 3.4–5.6 | 5.4–6.3 | 3.1 |
| Histidine | 0.8–1.1 | 1.1 | 0.4 | 0.7 | 2.2–2.4 | 1.0 |
| Arginine | 8.8–9.6 | 10.2 | 1.1 | 8.0–8.6 | 5.2–7.1 | 6.4 |

Example 7

Preparation of a Water-Soluble/Dispersible Poly (succinimide) Compound

The general synthetic route to the water-dispersible/soluble poly(succinimide) is described below using an example of a cationic poly(succinimide). To a 500 mL 3- or 4-necked round bottom flask equipped with overhead mechanical stirrer, oil bath with temperature controller, nitrogen line and reflux condenser, was added DMSO. Poly(succinimide) was dried at 120° C. for at least 1 hour, then added to the DMSO to achieve a solution of 20% solids. The poly(succinimide) solution was stirred and heated until all polymer dissolved (usually around 50–55° C.), and dimethyl amino propyl amine was added slowly to the reaction. The reaction was maintained at 60° C. with stirring, under nitrogen, overnight, and periodically titrated as above for free amine concentration.

After completion, the reaction was allowed to cool to room temperature, and transferred to a pressure reactor. The reaction mixture is exposed to $CH_3Cl$ gas. The pressure in the reactor is measured and the reaction is allowed to proceed until the pressure no longer changes. The reactor is depressurized and the resulting solution is transferred to a separatory funnel.

The reaction mixture was slowly added dropwise to a large excess of ethyl acetate with vigorous mechanical stirring. The viscous precipitate was suspended in acetone, stirred and broken up by hand. A mechanical homogenizer was used to reduce the particle size of the product, which allowed better extraction of the DMSO from the polymer in acetone. The powdered and granular products were isolated by vacuum filtration and dried overnight at 60° C. The polymers were then ground using a mortar and pestle, resuspended in acetone, homogenized (if the particle size was still large), filtered and dried again.

Example 8

Preparation of a Water-soluble/dispersible Functionalized Poly(succinimide)

To a 500 mL 3- or 4-necked round bottom flask equipped with overhead mechanical stirrer, oil bath with temperature controller, nitrogen line and reflux condenser, was added DMSO. Twenty grams of poly(succinimide) (weight average molecular weight of 4,500) was dried at 120° C. for at least 1 hour, then added to the DMSO to achieve a solution of 20% solids. The PSI solution was stirred and heated until all polymer dissolved (usually around 50–55° C.), and 6.9 grams 1-naphthalenemethylamine was added dropwise to the reaction with stirring. The oil bath was brought to 60° C. and maintained, and the reaction was allowed to continue with stirring, under nitrogen, overnight. The reaction was periodically checked for completion by withdrawing about 1.5 g of the reaction mixture and titrating it against 0.1 N hydrochloric acid to determine the concentration of free amine remaining. After 20–26 hours, the free amine concentration leveled off around 20–25%, and 11.9 grams N-methyl-D-glucamine was added slowly to the reaction. The reaction was maintained at 60° C. with stirring, under nitrogen, overnight, and periodically titrated as above for free amine concentration. After 22–26 hours, the total free amine concentration leveled at about 65%. The reaction was allowed to cool to room temperature, and transferred to a separatory funnel.

The reaction mixture was slowly added dropwise to a large excess of ethyl acetate with vigorous mechanical stirring. The viscous precipitate was suspended in acetone, stirred and broken up by hand. A mechanical homogenizer was used to reduce the particle size of the product, which allowed better extraction of the DMSO from the polymer in acetone. The powdered and granular products were isolated by vacuum filtration and dried overnight at 60° C. The polymers were then ground using a mortar and pestle, resuspended in acetone, homogenized (if the particle size was still large), filtered and dried again.

The following examples illustrate methods for employing the polyimido compounds to treat proteinaceous substrates. Although these examples describe a two-step method, the examples can also be carried out using the one-step method.

Example 9

Protection of Hair from Oxidation

A polymer containing the following antioxidant was prepared.

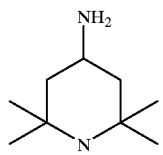

-continued

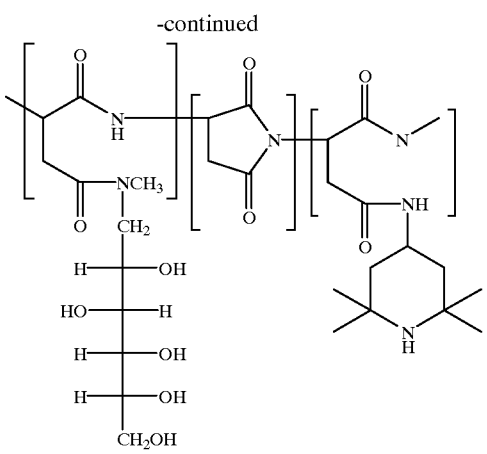

A tress of intact brown European hair was treated with a 10% (mass) aqueous solution of the polymer for 20 minutes. The treated tress was transferred to a pH=10 buffer solution at 45° C. for 30 minutes. The hair was then washed 10 times in a 10% (mass) aqueous solution of sodium lauryl sulfate. The wetting force of the treated hair was 0.00049. The untreated hair gave a wetting force of 0.00015. This increase in wetting force after 10 washes demonstrates the permanence of attachment of the polymer and delivery of the antioxidant to hair. Such a polymer would be amenable to a catalyzed process of the current invention where the nucleophilic catalytic agent is not an oxidant.

Example 10

Ultraviolet Protection of Hair

The polyimide containing the ultraviolet functionalizing moiety shown below was used in this example.

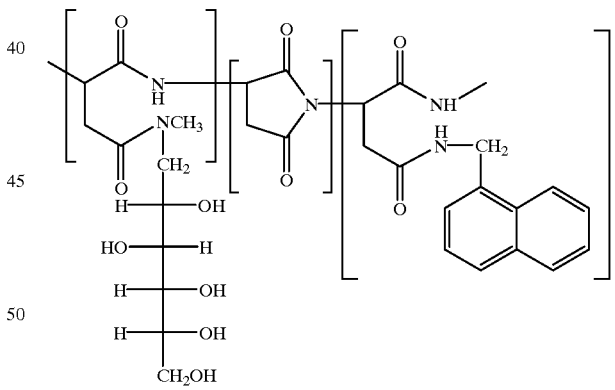

UV max 280, molar absorptivity 8120L/(mol cm)
Structure IV in which the water-solubilizing saccharide (W) is present at approximately 30 mole %, the UV chromophore is present at approximately 20 mole %, and the unreacted succinimide moieties are present at approximately 50 mole % in a polymer of approximately 30,000 Mw was applied to hair in the following manner. A tress of intact brown European hair was treated with a 10% (mass) aqueous solution of the polymer for 20 minutes. The treated tress was transferred to a pH=10 buffer solution at 45° C. for 30 minutes. The hair was then washed 10 times in a 10% (mass) aqueous solution of sodium lauryl sulfate. The wetting force of the treated hair was 0.00056. The untreated hair gave a wetting force of 0.00015. This increase in wetting force after 10 washes demonstrates the permanence of attachment of the polymer and delivery of the ultraviolet absorber to hair.

Example 11

Internal Modification of Damaged Hair Using Water-soluble/dispersible Polysuccinimides Hair that has been bleached and/or permed is chemically damaged. The chemical damage is the result of cleavage of the sulfur-sulfur cross-linkages and alkaline cleavage of amide linkages in the protein chains of the hair. which frequently fail to reform completely. As a result, hair is weakened. The strength or weakness of the hair can be measured as a function of its ability to withstand stretching to an additional 20% of its original length, i.e. damaged hair is relatively easy to extend 20% whereas intact hair requires much more work to extend an additional 20%. In this experiment, the extent to which the strength of chemically damaged (bleach/perm) hair can be rebuilt was measured. Hair strength was measured by measuring the work required to extend the hair an additional 20% of its length.

Four polymers were prepared with the compositions set out below. The molecular weights of the starting poly (succinimide) were 1100, 2500, and 4500. Each molecular weight was derivatized with 50 mole % ethanolamine. Additionally, the Mw=2500 starting poly(succinimide) was derivatized with 50 mole % DMAPA (Cl-quat). There were three treatment conditions studied: 1) 60 minute soak of hair in polymer solution followed by a soak in a pH=10 buffer solution, at 45° C., for 30 minutes, 2) bleached permed 60 minute soak of hair in polymer solution followed by soak in a solution of poly(ethyleneimine) Mw=750,000 (5% by mass, pH=10.8), at 45° C., 30 minutes, 3) 60 minute soak of hair in polymer solution followed by a soak in a solution of hexamethylene diamine, at 45° C., for 30 minutes. Additionally, three concentrations of hexamethylene diamine were tested: 0.22%, 2.2%, and 4.4% (mass%, pH=10–11.5). Control experiments were performed for each different process. These control experiments consisted of substitution of the polymer treatment with a 60 minute soak in pH=5.4 buffer (pH of water-soluble/dispersible-reactive derivative) followed by the identical treatment as described in 1), 2), and 3) above.

TABLE 1

Composition of Reparative Polymers

| Mol Wt. | Water-solubilizing Group | Water-solubilizing Group (mole %) | % Imide (mole %) |
|---|---|---|---|
| 1100 | Ethanolamine | 50 | 50 |
| 2500 | Ethanolamine | 50 | 50 |
| 4500 | Ethanolamine | 50 | 50 |
| 2500 | DMAPA Quat | 50 | 50 |

Results

Table 1 tabulates the data, and the 20% index for the hair treatment process using a buffer. The 20% index is defined as the ratio of the work to 20% extension after treatment to the work to 20% extension before treatment. The work to 20% extension before treatment is taken as the value for bleach/perm hair.

Table 2 tabulates the data and the 20% index

TABLE 2

| Treatment | Average Work to 20% Extension (Gm cm) | Standard Deviation (Gm cm) | 20% Index |
|---|---|---|---|
| A Virgin Brown Hair | 95.9 | — | — |
| B Bleached/Permed Hair | 42.3 | — | 1 |
| C B + Buffer Process Control | 42.6 | 26.7 | 1.007 |
| D B + Mw = 1100 Neutral | 64.7 | 29.2 | 1.529 |
| E B + Mw = 2500 Neutral | 58.2 | 29 | 1.375 |
| F B + Mw = 2500 Cationic | 45.4 | 23.6 | 1.075 |
| G B + Mw = 4500 Neutral | 41.7 | 24.8 | 0.9858 |

Comparison of A and B demonstrates the well-known degradation of tensile properties of hair upon chemical processing. Comparison of B and C demonstrates that the buffer treatment process has no impact on the tensile properties of damaged hair. Comparison between D, E, and G show the relation between performance and molecular weight. Comparisons of E and F show the impact of a cationic charge. The neutral material (E) shows a 20% Index significantly>1 while the cationic one (F) shows a 20% index only slightly>1.

These data allow the following conclusions. In order to be effective in improving the strength of damaged hair, the polymers should have a molecular weight<4500. Optimally the polymer should have a molecular weight in the range 1100–2500. The polymer should not be cationic in charge.

Table 3 tabulates the data, and the 20% index for hair treatments using a multifunctional amine as a combination pH adjuster and cross-linking agent.

TABLE 3

| Treatment | Average Work to 20% Extension (Gm cm) | Standard Deviation (Gm cm) | 20% Index |
|---|---|---|---|
| A Virgin Brown Hair | 95.9 | — | — |
| B Bleached/Permed Hair | 42.3 | — | 1 |
| H PEI Control | 69.5 | 33 | 1.64 |
| I Mw = 2500 Neutral PEI | 69.4 | 34.8 | 1.64 |
| J HMD Control | 53.7 | 25.2 | 1.26 |
| K Mw = 2500 Neutral mid HMD | 95.8 | 41.4 | 2.26 |
| L Mw = 1100 Neutral mid HMD | 89.7 | 44 | 2.12 |
| M Mw = 4500 Neutral mid HMD | 52.7 | 42 | 1.24 |
| N Mw = 2500 Neutral low HMD | 58.9 | 32 | 1.39 |
| O Mw = 2500 Neutral High HMD | 68.4 | 20 | 1.61 |

Comparison between B and H demonstrates that control treatment with poly(ethyleneimine) Mw=750000 shows a positive impact on the work to 20% extension. Comparison between H and I shows no benefit to the addition of the water-solubleldispersible reactive derivative. Comparison between B and J demonstrates that the control treatment with hexamethylene diamine shows a positive impact on the work to 20% extension. However addition of the water-soluble/dispersible reactive derivative of poly(succinimide) shows a dramatic improvement over this control. Comparison between K, L, and M again demonstrates the performance as a function of molecular weight. Comparisons between K, N, and O demonstrate that there is an optimum concentration of hexamethylene diamine.

These data allow the following conclusions. The multifunctional amine should be low in molecular weight. There is an optimum concentration of the multifunctional amine. The polymer should have molecular weight<4500. Optimally the polymer should have a molecular weight in the range 1100–2500.

While a number of embodiments of this invention have been represented, it is apparent that the basic construction can be altered to provide other embodiments which utilize the invention without departing from the spirit and scope of the invention. All such modifications and variations are intended to be included within the scope of the invention as defined in the appended claims rather than the specific embodiments which have been presented by way of example.

We claim:

1. A two-part system useful for treating a proteinaceous substrate which comprises a first part comprising a polyimido compound and a second part comprising an aqueous solution of a nucleophilic catalytic agent, wherein the pH value of the aqueous solution of nucleophilic catalytic agent is such that when the aqueous nucleophilic catalytic agent is mixed with the polyimido compound, the resulting mixture will have a pH in a range sufficient to enable the nucleophilic catalytic agent to covalently bond with the polyimido compound;

wherein the polyimido compound is selected from the group consisting of polysuccinimide compounds represented by Formula (1):

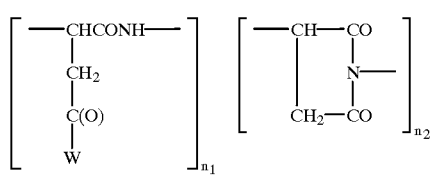

(1)

polyglutimide compounds represented by Formula (2);

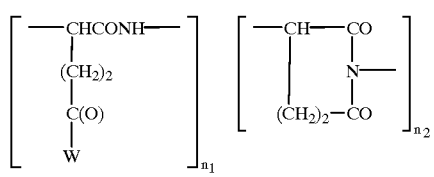

(2)

polysuccinimide compounds represented by Formula (3):

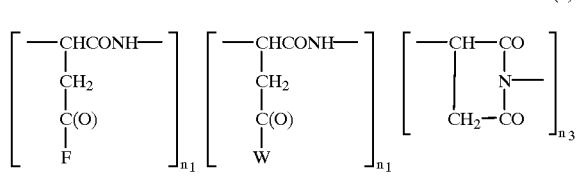

(3)

polyglutimide compounds represented by Formula (4);
pH in a range sufficient to enable the nucleophilic catalytic agent to covalently bond with the polyimido compound; and (b) contacting the mixture from step (a) with a proteinaceous substrate for a time sufficient to allow the mixture to react with the proteinaceous substrate;

wherein the polyimido compound is selected from the group consisting of polysuccinimide compounds represented by Formula (1):

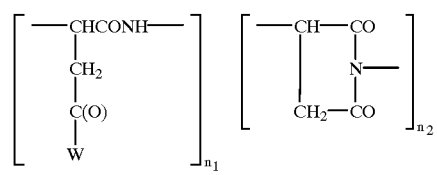

(1)

polyglutimide compounds represented by Formula (2);

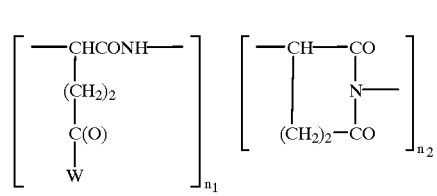

(2)

polysuccinimide compounds represented by Formula (3);

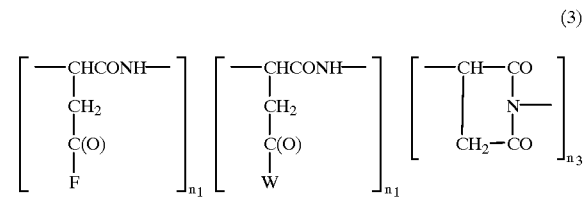

(3)

polyglutimide compounds represented by Formula (4);

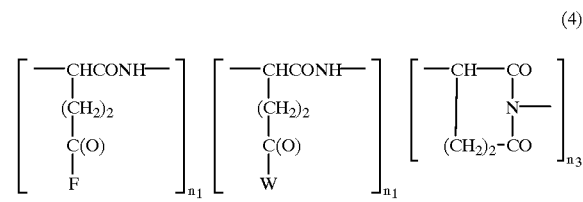

(4)

copolymers of the polysuccinimide compounds represented by Formula (1) with the polyglutimide compounds represented by Formula (2); and copolymers of the polysuccinimide compounds represented by Formula (3) with the polyglutimide compounds represented by Formula (4);

wherein W is a water-solubilizing/dispersing moiety that provides water-solubility and/or water-dispersibility to the polyimido compound; F is a functionalizing moiety that provides functionality to the polyimido compound; the ratio of $n_1$ to $n_2$ is from about 1:99 to about 99:1; the ratio of $n_3:n_4:n_5$ is from about 1:1:98 to about 45:45:10; and the molecular weight of the polyimido compound is from about 300 to about 1,000,000.

2. The two-part system according to claim 1, wherein W is derived from a nucleophilic moiety selected from the group consisting of amines, alcohols, phenols, thiols, and carboxylates.

3. The two-part system according to claim 2, wherein W is selected from the group consisting of:

(1) aminopolysaccharides represented by the formula, —N($R_1$)-polysaccharide, wherein $R_1$ is hydrogen or lower alkyl and the number of units in the polysaccharide ranges from 1 to about 51;

(2) amines containing quaternary ammonium salts represented by the formula, [—N($R_1$)($CH_2$)$_{n3}$N$^+$($CH_3$)$_3$]

[A$^-$], wherein R$_1$ is hydrogen or lower alkyl, n$_3$ is an integer from 1 to about 10, and A is a monovalent anion;

(3) amines containing alcohols represented by the formula, —N(R$_1$)(CH$_2$)$_{n_4}$OH, wherein R$_1$ is hydrogen or lower alkyl and n$_4$ is an integer from 2 to about 10;

(4) amines containing polyalkoxylated alcohols represented by the formula, —N(R$_1$)CH(CH$_3$)CH$_2$—(OCHR$_2$CH$_2$)$_{n_5}$—OCH$_3$, wherein R$_1$ is hydrogen or lower alkyl, R$_2$ may be hydrogen or methyl, and n$_5$ is an integer from 0 to about 50;

(5) thiols containing alcohols represented by the formula, —S(CH$_2$)$_{n_6}$OH, wherein n$_6$ is an integer ranging from 2 to about 10;

(6) alcohols containing ethers represented by the formula, —O(CH$_2$CH$_2$O)$_{n_7}$OM, wherein n$_7$ is an integer ranging from 0 to about 50 and M is an alkyl group containing from 1 to about 30 carbons;

(7) —O$^-$X$^+$, where X is selected from the group consisting of H$^+$, Na$^+$, Li$^+$, NH$_4^+$, NH(CH$_3$)$_3^+$; NH$_3$(CH$_2$CH$_2$OH)$^+$, NH$_2$(CH$_2$CH$_2$OH)$_2^+$, and NH(CH$_2$CH$_2$OH)$_3^+$;

(8) [—NH(CH$_2$)$_3$N$^+$(CH$_3$)$_2$CH$_2$COONa][A$^-$], —N(CH$_3$)(CH$_2$)$_2$SO$_3$Na, and —NH(CH$_2$)$_2$SO$_3$Na, wherein A is a monovalent anion.

4. The two-part system according to claim 1, wherein F is derived from a nucleophilic moiety selected from the group consisting of amines, alcohols, phenols, thiols, and carboxylates.

5. The two-part system according to claim 4, wherein F is selected from the group consisting of antimicrobials, ultraviolet chromophores, dyes, anti-oxidants, fluorescing agents, brightening agents, shine and gloss enhancers, softening agents, conditioning agents, water-repellants, and charge-modifiers.

6. The two-part system according to claim 1, wherein the ratio of n$_1$ to n$_2$ is from about 95:5 to about 5:95.

7. The two-part system according to claim 1, wherein the ratio of n$_3$:n$_4$:n$_5$ is from about 5:5:90 to about 40:40:20.

8. The two-part system according to claim 1, wherein the molecular weight of the polyimido compound is from about 300 to about 5000.

9. The two-part system according to claim 1, wherein the molecular weight of the polyimido compound is greater than about 5000.

10. The two-part system according to claim 1, wherein the polyimido compound is a polysuccinimide represented by Formula (1).

11. The two-part system according to claim 1, wherein the polyimido compound is a polyglutimide represented by Formula (2).

12. The two-part system according to claim 1, wherein the polyimido compound is a polysuccinimide represented by Formula (3).

13. The two-part system according to claim 1, wherein the polyimido compound is a polyglutimide represented by Formula (4).

14. The two-part system according to claim 1, wherein the nucleophilic catalytic agent is selected from the group consisting of pyridines, tertiary amines, thiols, and peroxides.

15. The two-part system according to claim 1, wherein the imide group of the polyimido compound and the nucleophilic catalytic agent are present in a molar ratio from about 1:0.01 to about 1:10.

16. The two-part system according to claim 1, wherein the pH value of the aqueous solution of nucleophilic catalytic agent is greater than about 6.

17. The two-part system according to claim 1, further comprising an agent selected from the group consisting of alkali sulfites, alkali bisulfites, hydrogen peroxide, organic peroxides, organic thiols, alkali salts of thioglycolic acid, and alkaline salts of thioglycolic acid.

18. A method for treating a proteinaceous substrate which comprises the steps of:

(a) contacting a polyimido compound with an aqueous of solution an nucleophilic catalytic agent to form a mixture, wherein the pH value of the aqueous solution of nucleophilic catalytic agent is such that when the aqueous nucleophilic catalytic agent is mixed with the polyimido compound, the resulting mixture will have a pH in a range sufficient to enable the nucleophilic catalytic agent to react with the polyimido compound; and (b) contacting the mixture from step (a) with a proteinaceous substrate for a time sufficient to allow the mixture to react with the proteinaceous substrate;

wherein the polyimido compound is selected from the group consisting of polysuccinimide compounds represented by Formula (1):

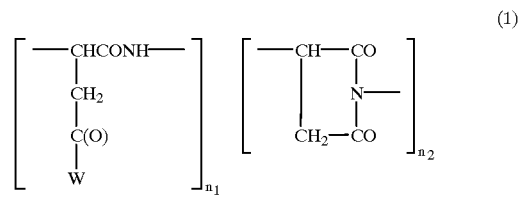

polyglutimide compounds represented by Formula (2);

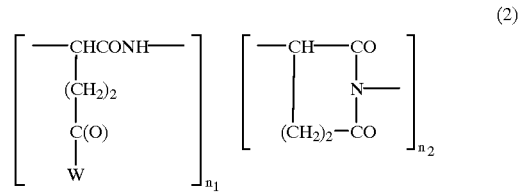

polysuccinimide compounds represented by Formula (3):

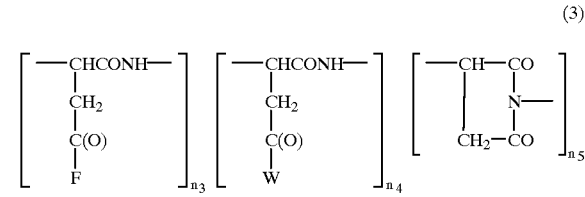

polyglutimide compounds represented by Formula (4);

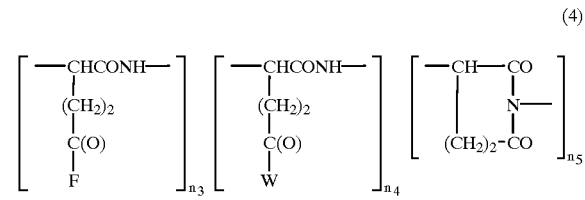

copolymers of the polysuccinimide compounds represented by Formula (1) with the polyglutimide compounds represented by Formula (2); and copolymers of the polysuccinimide compounds represented by Formula (3) with the polyglutimide compounds represented by Formula (4);

wherein W is a water-solubilizing/dispersing moiety that provides water-solubility and/or water-dispersibility to the polyimido compound; F is a functionalizing moiety that provides functionality to the polyimido compound; the ratio of $n_1$ to $n_2$ is from about 1:99 to about 99:1; the ratio of $n_3:n_4:n_5$ is from about 1:1:98 to about 45:45:10; and the molecular weight of the polyimido compound is from about 300 to about 1,000,000.

19. The method according to claim 18, wherein W is derived from a nucleophilic moiety selected from the group consisting of amines, alcohols, phenols, thiols, and carboxylates.

20. The method according to claim 19, wherein W is selected from the group consisting of:

(1) aminopolysaccharides represented by the formula, —N($R_1$)-polysaccharide, wherein $R_1$ is hydrogen or lower alkyl and the number of units in the polysaccharide ranges from 1 to about 51;

(2) amines containing quaternary ammonium salts represented by the formula, [—N($R_1$)($CH_2$)$_{n3}$N$^+$($CH_3$)$_3$][A$^-$], wherein $R_1$ is hydrogen or lower alkyl, $n_3$ is an integer from 1 to about 10, and A is a monovalent anion;

(3) amines containing alcohols represented by the formula, —N($R_1$)($CH_2$)$_{n4}$OH, wherein $R_1$ is hydrogen or lower alkyl and $n_4$ is an integer from 2 to about 10;

(4) amines containing polyalkoxylated alcohols represented by the formula, —N($R_1$)CH($CH_3$)$CH_2$—(OCHR$_2$CH$_2$)$_{n5}$—OCH$_3$, wherein $R_1$ is hydrogen or lower alkyl, $R_2$ may be hydrogen or methyl, and $n_5$ is an integer from 0 to about 50;

(5) thiols containing alcohols represented by the formula, —S($CH_2$)$_{n6}$OH, wherein $n_6$ is an integer ranging from 2 to about 10;

(6) alcohols containing ethers represented by the formula, —O($CH_2CH_2$O)$_{n7}$OM, wherein $n_7$ is an integer ranging from 0 to about 50 and M is an alkyl group containing from 1 to about 30 carbons;

(7) —O$^-$X$^+$, where X is selected from the group consisting of H$^+$, Na$^+$, Li$^+$, NH$_4$$^+$, NH(CH$_3$)$_3$$^+$; NH$_3$(CH$_2$CH$_2$OH)$^+$, NH$_2$(CH$_2$CH$_2$OH)$_2$$^+$, and NH(CH$_2$CH$_2$OH)$_3$$^+$;

(8) [—NH($CH_2$)$_3$N$^+$($CH_3$)$_2$$CH_2$COONa][A$^-$], —N(CH$_3$)(CH$_2$)$_2$SO$_3$Na, and —NH($CH_2$)$_2$SO$_3$Na, wherein A is a monovalent anion.

21. The method according to claim 18, wherein F is derived from a nucleophilic moiety selected from the group consisting of amines, alcohols, phenols, thiols, and carboxylates.

22. The method according to claim 21, wherein F is selected from the group consisting of antimicrobials, ultraviolet chromophores, dyes, anti-oxidants, fluorescing agents, brightening agents, shine and gloss enhancers, softening agents, conditioning agents, water-repellants, and charge-modifiers.

23. The method according to claim 18, wherein the ratio of $n_1$ to $n_2$ is from about 95:5 to about 5:95.

24. The method according to claim 18, wherein the ratio of $n_3:n_4:n_5$ is from about 5:5:90 to about 40:40:20.

25. The method according to claim 18, wherein the molecular weight of the polyimido compound is from about 300 to about 5000.

26. The method according to claim 18, wherein the molecular weight of the polyimido compound is greater than about 5000.

27. The method according to claim 18, wherein the polyimido compound is a polysuccinimide represented by Formula (1).

28. The method according to claim 18, wherein the polyimido compound is a polyglutimide represented by Formula (2).

29. The method according to claim 18, wherein the polyimido compound is a polysuccinimide represented by Formula (3).

30. The method according to claim 18, wherein the polyimido compound is a polyglutimide represented by Formula (4).

31. The method according to claim 18, wherein the nucleophilic catalytic agent is selected from the group consisting of pyridines, tertiary amines, thiols, and peroxides.

32. The method according to claim 18, wherein the polyimido compound and the nucleophilic catalytic agent are present in a ratio from about 1:0.01 to about 1:10.

33. The method according to claim 18, wherein the pH value of the aqueous solution of nucleophilic catalytic agent is greater than about 6.

34. The method according to claim 18, wherein the proteinaceous substrate is selected from the group consisting of hair, wool, skin, leather, silk, fur, felt, and nails.

35. The method according to claim 18, wherein the polyimido compound is cross-linked to a multifunctional nucleophilic agent.

36. The method according to claim 35, wherein the multifunctional nucleophilic agent is selected from the group consisting of 1,6-hexamethylenediamine, low-molecular weight polyethyleneimines, polyalkoxides, and polythiols.

37. The method according to claim 18, wherein the water-solubilizing/dispersing moiety bears an ionic charge and is electrostatically bound to a moiety bearing the opposite charge.

38. The method according to claim 37, wherein the moiety bearing the opposite charge is selected from the group consisting of antimicrobials, ultraviolet chromophores, anionic dyes, anti-oxidants, fluorescing agents, brightening agents, shine and gloss enhancers, softening agents, and conditioning agents.

39. The method according to claim 18, further comprising an agent selected from the group consisting of alkali sulfites, alkali bisulfites, hydrogen peroxide, organic peroxides, organic thiols, alkali salts of thioglycolic acid, and alkaline salts of thioglycolic acid.

40. A composition useful for treating a proteinaceous substrate which comprises an aqueous mixture of a polyimido compound and a nucleophilic catalytic agent having a pH value in a range sufficient to enable the nucleophilic catalytic agent to covalently bond with the polyimido compound;

wherein the polyimido compound is selected from the group consisting of polysuccinimide compounds represented by Formula (1):

(1)

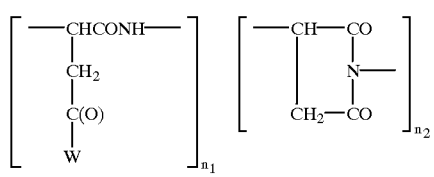

polyglutimide compounds represented by Formula (2);

(2)

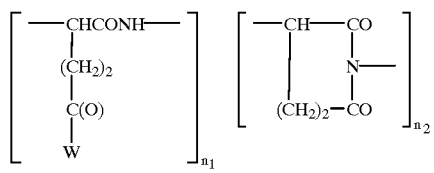

polysuccinimide compounds represented by Formula (3):

(3)

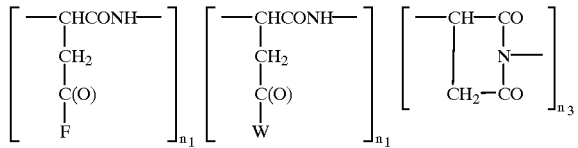

polyglutimide compounds represented by Formula (4);

(4)

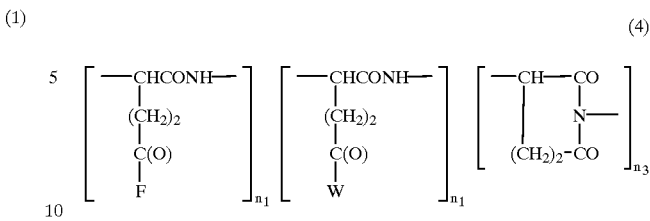

copolymers of the polysuccinimide compounds represented by Formula (1) with the polyglutimide compounds represented by Formula (2); and copolymers of the polysuccinimide compounds represented by Formula (3) with the polyglutimide compounds represented by Formula (4);

wherein W is a water-solubilizing/dispersing moiety that provides water-solubility and/or water-dispersibility to the polyimido compound; F is a functionalizing moiety that provides functionality to the polyimido compound; the ratio of $n_1$ to $n_2$ is from about 1:99 to about 99:1; the ratio of $n_3$:$n_4$:$n_5$ is from about 1:1:98 to about 45:45:10; and the molecular weight of the polyimido compound is from about 300 to about 1,000,000.

41. A method for treating a proteinaceous substrate which comprises the steps of:
    (a) contacting an imido or polyimido compound with an aqueous solution of an nucleophilic catalytic agent to form a mixture, wherein the pH value of the aqueous solution of nucleophilic catalytic agent is such that when the aqueous nucleophilic catalytic agent is mixed with the imido or polyimido compound, the resulting mixture will have a pH in a range sufficient to enable the nucleophilic catalytic agent to covalently bond with the imido or polyimido compound; wherein the imido or polyimido compound has attached thereto a functionalizing moiety F that provides functionality to the imido or polyimido compound; and
    (b) contacting the mixture from step (a) with a proteinaceous substrate for a time sufficient to allow the mixture to react with the proteinaceous substrate.

\* \* \* \* \*